US012768323B2

(12) United States Patent
Hauser et al.

(10) Patent No.: US 12,768,323 B2
(45) Date of Patent: Oct. 20, 2026

(54) VEHICLE FUEL MONITORING SYSTEM AND METHODS

(71) Applicant: Donaldson Company, Inc., Bloomington, MN (US)

(72) Inventors: Bradly G. Hauser, Minneapolis, MN (US); Chad M. Goltzman, Bloomington, MN (US); Michael J. Wynblatt, Minneapolis, MN (US)

(73) Assignee: Donaldson Company, Inc., Bloomington, MN (US)

( * ) Notice: Subject to any disclaimer, the term of this patent is extended or adjusted under 35 U.S.C. 154(b) by 1101 days.

(21) Appl. No.: 17/789,292

(22) PCT Filed: Jan. 29, 2021

(86) PCT No.: PCT/US2021/015866
§ 371 (c)(1),
(2) Date: Jan. 4, 2023

(87) PCT Pub. No.: WO2021/155255
PCT Pub. Date: Aug. 5, 2021

(65) Prior Publication Data

US 2023/0044784 A1 Feb. 9, 2023

Related U.S. Application Data

(60) Provisional application No. 62/967,369, filed on Jan. 29, 2020.

(51) Int. Cl.
*F02M 37/40* (2019.01)
*B01D 35/00* (2006.01)
(Continued)

(52) U.S. Cl.
CPC ........... *F02M 37/40* (2019.01); *B01D 35/005* (2013.01); *B01D 35/1435* (2013.01);
(Continued)

(58) Field of Classification Search
CPC .. F02M 37/40; B01D 35/005; B01D 35/1435; G01N 15/0826; G01N 33/2847;
(Continued)

(56) References Cited

U.S. PATENT DOCUMENTS 6,971,258 B2 12/2005 Rhodes et al.
7,275,415 B2 10/2007 Rhodes et al.
(Continued)

FOREIGN PATENT DOCUMENTS

CN 110344970 10/2019
DE 102008034349 1/2010
(Continued)

OTHER PUBLICATIONS

"International Preliminary Report on Patentability," for PCT Patent Application No. PCT/US2022/038722 mailed Feb. 8, 2024 (10 pages).
(Continued)

*Primary Examiner* — Tyler D Paige
(74) *Attorney, Agent, or Firm* — Pauly, DeVries Smith & Deffner LLC

(57) ABSTRACT

Embodiments herein relate to fuel monitoring systems and related methods. In an embodiment, a fuel monitoring system for a vehicle is included having a fuel filter sensor device configured to generate data reflecting a filter restriction value of a fuel filter, a geolocation circuit configured to generate or receive geolocation data, and a system control circuit configured to evaluate the sensor data to determine changes in the filter restriction value. The control circuit can receive fuel level data, cross-reference geolocation data and fuel level data to identify refueling locations utilized, and correlate refueling locations with subsequent changes in filter restriction to identify an effect of specific refueling locations on fuel filter loading. In some embodiments, a
(Continued)

refueling guidance system for a vehicle is included that can provide route and/or refueling site recommendations based on fuel filter loading rate data. Other embodiments are also included herein.

18 Claims, 11 Drawing Sheets

(51) Int. Cl.

| | |
|---|---|
| ***B01D 35/143*** | (2006.01) |
| ***G01N 15/08*** | (2006.01) |
| ***G01N 33/28*** | (2006.01) |
| ***G06Q 30/0601*** | (2023.01) |
| ***G07C 5/00*** | (2006.01) |
| *G07C 5/08* | (2006.01) |

(52) U.S. Cl.
CPC ..... *G01N 15/0826* (2013.01); *G06Q 30/0631* (2013.01); *G07C 5/008* (2013.01); *G01N 33/2847* (2013.01); *G07C 5/0825* (2013.01); *G07C 5/0833* (2013.01)

(58) Field of Classification Search
CPC ......... G01N 2015/084; G06Q 30/0631; G06Q 50/06; G06Q 50/40; G06Q 10/047; G07C 5/008; G07C 5/0825; G07C 5/0833
USPC ......................................................... 701/31.4
See application file for complete search history.

(56) References Cited

U.S. PATENT DOCUMENTS

| | | | |
|---|---|---|---|
| 9,874,509 B2 | 1/2018 | Yacoub et al. | |
| 10,006,883 B2 | 6/2018 | Sugiyama et al. | |
| 10,119,886 B2 | 11/2018 | Dhingra et al. | |
| 10,330,579 B2 | 6/2019 | Sugiyama et al. | |
| 10,359,408 B2 | 7/2019 | Dial | |
| 10,366,547 B2 * | 7/2019 | Frankowski | G06Q 10/00 |
| 10,753,301 B2 * | 8/2020 | Prabhala | B01D 35/143 |
| 2007/0150369 A1 | 6/2007 | Zivin | |
| 2008/0229720 A1 | 9/2008 | Benscoter et al. | |
| 2009/0005974 A1 | 1/2009 | Lenneman et al. | |
| 2014/0121967 A1 | 5/2014 | Anbalagan et al. | |
| 2016/0068077 A1 * | 3/2016 | Smith | H01M 8/04089<br>429/410 |
| 2016/0208726 A1 | 7/2016 | Tanaka et al. | |
| 2016/0280160 A1 | 9/2016 | MacNeille et al. | |
| 2018/0114378 A1 | 4/2018 | Slusar | |
| 2018/0174375 A1 | 6/2018 | Frankowski et al. | |
| 2018/0340784 A1 | 11/2018 | Upadhyay et al. | |
| 2019/0003365 A1 | 1/2019 | Dhanraj | |
| 2019/0154453 A1 | 5/2019 | Leone et al. | |
| 2019/0283524 A1 | 9/2019 | Kopfstein | |
| 2020/0043068 A1 | 2/2020 | McQuade et al. | |
| 2023/0044784 A1 * | 2/2023 | Hauser | B01D 35/1435 |
| 2023/0068962 A1 * | 3/2023 | Zambon | B01D 46/0086 |
| 2023/0213428 A1 | 7/2023 | Khanna et al. | |
| 2023/0256373 A1 | 8/2023 | Johnson et al. | |

FOREIGN PATENT DOCUMENTS

| | | |
|---|---|---|
| DE | 102019102880 | 8/2019 |
| EP | 2312413 | 4/2013 |
| EP | 3628388 | 4/2020 |
| EP | 3628972 | 4/2020 |
| GB | 2529181 | 2/2016 |
| JP | 2017020464 | 1/2017 |
| WO | 2017176982 | 10/2017 |
| WO | 2019232305 | 12/2019 |
| WO | 2021155255 | 8/2021 |
| WO | 2023009753 | 2/2023 |

OTHER PUBLICATIONS

"Non-Final Office Action," for U.S. Appl. No. 17/876,368 mailed Nov. 27, 2024 (30 pages).
"International Preliminary Report on Patentability," for PCT Application No. PCT/US2021/015866 mailed Aug. 11, 2022 (11 pages).
"International Search Report and Written Opinion," for PCT Application No. PCT/US2021/015866 mailed Jul. 19, 2021 (17 pages).
"Invitation to Pay Additional Fees," for PCT Application No. PCT/US2021/015866 mailed May 26, 2021 (13 pages).
"Communication pursuant to Article 94(3) EPC," for European Patent Application No. 22755368.2 mailed May 30, 2025 (4 pages).
"Final Office Action," for U.S. Appl. No. 17/876,368 mailed May 6, 2025 (28 pages).
"Response to Non-Final Rejection," mailed on Nov. 27, 2024, for U.S. Appl. No. 17/876,368, submitted via Patent Center on Feb. 14, 2025, 13 pages.
"International Search Report and Written Opinion," for PCT Application No. PCT/US2022/038722 mailed Dec. 1, 2022 (15 pages).
"Extended European Search Report," for European Patent Application No. 25165515.5 mailed Sep. 23, 2025 (5 pages).
"Non-Final Office Action," for U.S. Appl. No. 17/876,368 mailed Oct. 31, 2025 (31 pages).
"Response to Final Rejection," mailed on May 6, 2025, for U.S. Appl. No. 17/876,368), submitted via Patent Center on Jul. 29, 2025, 16 pages.
"Final Office Action," for U.S. Appl. No. 17/876,368 mailed May 12, 2026 (17 pages).

* cited by examiner

VEHICLE FUEL MONITORING SYSTEM AND METHODS

This application is being filed as a PCT International Patent application on Jan. 29, 2021 in the name of Donaldson Company, Inc., a U.S. national corporation, applicant for the designation of all countries, and Bradly G. Hauser, a citizen of the U.S., Chad M. Goltzman, a citizen of the U.S. and Michael J. Wynblatt, a citizen of the U.S., inventors for the designation of all countries, and claims priority to U.S. Provisional Patent Application No. 62/967,369, filed Jan. 29, 2020, the contents of which are herein incorporated by reference in its entirety.

FIELD

Embodiments herein relate to fuel monitoring systems and vehicle refueling guidance systems and related methods.

BACKGROUND

Fuel filters remove impurities from fuel thereby preventing various adverse effects including fuel injector clogging. However, fuel filters have a finite useful life and must be replaced or otherwise serviced regularly. Fuel filters become saturated with impurities during use in a process known as filter loading. As filter loading increases, filter restriction increases. Therefore, filter restriction is commonly used as an indicator to determine when a filter, such as a fuel filter, needs to be replaced or otherwise serviced.

SUMMARY

Embodiments herein relate to fuel monitoring systems and vehicle refueling guidance systems and related methods. In a first aspect, a fuel monitoring system for a vehicle is included having a fuel filter sensor device configured to generate data reflecting a filter restriction value of a fuel filter, a geolocation circuit configured to generate or receive geolocation data, and a system control circuit configured to evaluate the sensor data to determine changes in the filter restriction value, receive fuel level data, cross-reference geolocation data and fuel level data to identify refueling locations utilized, and correlate refueling locations with subsequent changes in the filter restriction value to identify an effect of specific refueling locations utilized on fuel filter loading.

In a second aspect, in addition to one or more of the preceding or following aspects, or in the alternative to some aspects, the system control circuit is further configured to estimate expected loading rate associated with refueling at a particular refueling location based on previously observed fuel filter loading.

In a third aspect, in addition to one or more of the preceding or following aspects, or in the alternative to some aspects, the system control circuit is further configured to calculate a cost associated with a particular refueling location based on estimated expected fuel filter loading rate.

In a fourth aspect, in addition to one or more of the preceding or following aspects, or in the alternative to some aspects, the system control circuit is further configured to generate a recommendation can include a recommended refueling location.

In a fifth aspect, in addition to one or more of the preceding or following aspects, or in the alternative to some aspects, the recommendation is forwarded to a mobile communications device associated with a vehicle or a driver of a vehicle.

In a sixth aspect, in addition to one or more of the preceding or following aspects, or in the alternative to some aspects, the recommendation is formed including consideration of fuel system parts inventory at refueling locations.

In a seventh aspect, in addition to one or more of the preceding or following aspects, or in the alternative to some aspects, the system control circuit is further configured to generate a recommendation can include a recommended refueling time.

In an eighth aspect, in addition to one or more of the preceding or following aspects, or in the alternative to some aspects, the system control circuit is further configured to generate a recommendation can include a recommended refueling location and a recommended refueling time.

In a ninth aspect, in addition to one or more of the preceding or following aspects, or in the alternative to some aspects, the system control circuit is further configured to generate a listing of recommended and dis-recommended fueling stations.

In a tenth aspect, in addition to one or more of the preceding or following aspects, or in the alternative to some aspects, the system control circuit is further configured to generate an alert for a vehicle driver if the vehicle enters the location of a dis-recommended fueling station.

In an eleventh aspect, in addition to one or more of the preceding or following aspects, or in the alternative to some aspects, the system control circuit is further configured to generate a report that profiles the frequency with which different drivers in a fleet use recommended and dis-recommended fueling stations.

In a twelfth aspect, in addition to one or more of the preceding or following aspects, or in the alternative to some aspects, the fuel level data is received from a CANBus network.

In a thirteenth aspect, in addition to one or more of the preceding or following aspects, or in the alternative to some aspects, the fuel filter sensor device can include an upstream pressure sensor configured to sense a pressure in a fuel line upstream of the fuel filter and a downstream pressure sensor configured to sense a pressure in the fuel line downstream of the fuel filter.

In a fourteenth aspect, in addition to one or more of the preceding or following aspects, or in the alternative to some aspects, the geolocation circuit can include a satellite communications circuit.

In a fifteenth aspect, in addition to one or more of the preceding or following aspects, or in the alternative to some aspects, the geolocation circuit receives geolocation data from a separate device.

In a sixteenth aspect, in addition to one or more of the preceding or following aspects, or in the alternative to some aspects, the geolocation circuit infers geolocation based on detection of a wireless signal.

In a seventeenth aspect, in addition to one or more of the preceding or following aspects, or in the alternative to some aspects, the wireless signal can include at least one of a WIFI signal and a cellular communications tower signal.

In an eighteenth aspect, in addition to one or more of the preceding on following aspects, or in the alternative to some aspects, the effect of specific refueling locations on fuel filter loading is determined based on an effect on a filter loading curve.

In a nineteenth aspect, in addition to one or more of the preceding or following aspects, or in the alternative to some aspects, the system control circuit is configured to distinguish between a normal filter loading curve, an accelerated filter loading curve, and a sudden clogging curve.

In a twentieth aspect, in addition to one or more of the preceding or following aspects, or in the alternative to some aspects, the system control circuit is configured to distinguish between a normal filter loading curve and an abnormal filter loading curve.

In a twenty-first aspect, in addition to one or more of the preceding or following aspects, or in the alternative to some aspects, the system control circuit is configured to identify a refueling location visited immediately before an abnormal filter loading curve begins.

In a twenty-second aspect, in addition to one or more of the preceding or following aspects, or in the alternative to some aspects, the system control circuit is configured to identify a refueling location visited immediately before a filter loading curve changes to exhibit more rapid loading.

In a twenty-third aspect, in addition to one or more of the preceding or following aspects, or in the alternative to some aspects, the system control circuit classifies the identified location as being a source of contaminated fuel and stores the classification in a refueling location database.

In a twenty-fourth aspect, in addition to one or more of the preceding or following aspects, or in the alternative to some aspects, the system control circuit is further configured to generate a fuel system parts inventory recommendation based on the refueling location database.

In a twenty-fifth aspect, in addition to one or more of the preceding or following aspects, or in the alternative to some aspects, the fuel system parts inventory recommendation includes a recommendation to increase an inventory of fuel filters at refueling locations that occur in a sequence of refueling locations after an identified location with contaminated fuel.

In a twenty-sixth aspect, in addition to one or more of the preceding or following aspects, or in the alternative to some aspects, the system control circuit classifies the identified location as being a possible source of contaminated fuel and queries a database for additional data regarding the identified location.

In a twenty-seventh aspect, in addition to one or more of the preceding or following aspects, or in the alternative to some aspects, the system control circuit is configured to determine sequences of refueling locations visited immediately before a sudden clogging curve begins.

In a twenty-eighth aspect, in addition to one or more of the preceding or following aspects, or in the alternative to some aspects, the system control circuit is further configured to evaluate one or more of weather data, temperature data, pressure data, humidity data, fuel filter model number, engine model number, driver ID, and detected refueling times to identify the effect of specific refueling locations on fuel filter loading.

In a twenty-ninth aspect, in addition to one or more of the preceding or following aspects, or in the alternative to some aspects, cross-referencing geolocation data and fuel level data to identify refueling locations can include identifying a geolocation at a time of a fuel level increase.

In a thirtieth aspect, in addition to one or more of the preceding or following aspects, or in the alternative to some aspects, the system can further include a water-in-fuel sensor and the system control circuit can be configured to evaluate data from the water-in-fuel sensor and correlate refueling locations with subsequent changes in the data from the water-in-fuel sensor to identify an effect of specific refueling locations on water-in-fuel sensor data.

In a thirty-first aspect, in addition to one or more of the preceding or following aspects, or in the alternative to some aspects, the system can further include a particulate counter and the system control circuit further configured to evaluate data from the particulate counter and correlate refueling locations with subsequent changes in the data from the particulate counter to identify an effect of specific refueling locations on particulate counter data.

In a thirty-second aspect, in addition to one or more of the preceding or following aspects, or in the alternative to some aspects, the system control circuit can be configured to estimate remaining fuel filter life taking into account refueling locations used.

In a thirty-third aspect, in addition to one or more of the preceding or following aspects, or in the alternative to some aspects, the filter restriction value can include a pressure drop across the fuel filter.

In a thirty-fourth aspect, a method of monitoring fuel systems is included herein and can include measuring filter restriction of a fuel filter, identifying refueling locations based on fuel level data and geolocation data, and calculating an impact of specific refueling locations on fuel filter loading by evaluating filter restriction trends after refueling at refueling locations.

In a thirty-fifth aspect, in addition to one or more of the preceding or following aspects, or in the alternative to some aspects, a method further can include estimating expected loading rate associated with refueling at a particular refueling location based on previously observed fuel filter loading.

In a thirty-sixth aspect, in addition to one or more of the preceding or following aspects, or in the alternative to some aspects, a method further can include calculating a cost associated with a particular refueling location based on estimated expected fuel filter loading rate.

In a thirty-seventh aspect, in addition to one or more of the preceding or following aspects, or in the alternative to some aspects, a method further can include generating a recommendation can include a recommended refueling location.

In a thirty-eighth aspect, in addition to one or more of the preceding or following aspects, or in the alternative to some aspects, a method further can include forwarding the recommendation to a mobile communications device associated with a vehicle or a driver of a vehicle.

In a thirty-ninth aspect, in addition to one or more of the preceding or following aspects, or in the alternative to some aspects, a recommendation is generated including consideration of fuel system parts inventory at refueling locations.

In a fortieth aspect, in addition to one or more of the preceding or following aspects, or in the alternative to some aspects, a method further can include generating a recommendation can include a recommended refueling time.

In a forty-first aspect, in addition to one or more of the preceding or following aspects, or in the alternative to some aspects, a method further can include generating a recommendation can include a recommended refueling location and a recommended refueling time.

In a forty-second aspect, in addition to one or more of the preceding or following aspects, or in the alternative to some aspects, a method further can include forwarding the recommendation to a mobile communications device associated with a vehicle or a driver of a vehicle.

In a forty-third aspect, in addition to one or more of the preceding or following aspects, or in the alternative to some aspects, a method further can include generating a listing of recommended and dis-recommended fueling stations.

In a forty-fourth aspect, in addition to one or more of the preceding or following aspects, or in the alternative to some aspects, a method further can include generating an alert for a vehicle driver if the vehicle enters the location of a dis-recommended fueling station.

In a forty-fifth aspect, in addition to one or more of the preceding or following aspects, or in the alternative to some aspects, a method further can include generating a report that profiles the frequency with which different drivers in a fleet use recommended and dis-recommended fueling stations.

In a forty-sixth aspect, in addition to one or more of the preceding or following aspects, or in the alternative to some aspects, a method further can include distinguishing between a normal filter loading curve, an accelerated filter loading curve, and a sudden clogging curve.

In a forty-seventh aspect, in addition to one or more of the preceding or following aspects, or in the alternative to some aspects, a method further can include distinguishing between a normal filter loading curve and an abnormal filter loading curve.

In a forty-eighth aspect, in addition to one or more of the preceding or following aspects, or in the alternative to some aspects, a method further can include identifying a refueling location visited immediately before an abnormal filter loading curve begins.

In a forty-ninth aspect, in addition to one or more of the preceding or following aspects, or in the alternative to some aspects, a method further can include identifying a refueling location visited immediately before a filter loading curve changes to exhibit more rapid loading.

In a fiftieth aspect, in addition to one or more of the preceding or following aspects, or in the alternative to some aspects, a method further can include classifying the identified location as being a source of contaminated fuel and stores the classification in a refueling location database.

In a fifty-first aspect, in addition to one or more of the preceding or following aspects, or in the alternative to some aspects, a method further can include generating a fuel system parts inventory recommendation based on the refueling location database.

In a fifty-second aspect, in addition to one or more of the preceding or following aspects, or in the alternative to some aspects, a fuel system parts inventory recommendation includes a recommendation to increase an inventory of fuel filters at refueling locations that occur in a sequence of refueling locations after an identified location with contaminated fuel.

In a fifty-third aspect, in addition to one or more of the preceding or following aspects, or in the alternative to some aspects, a method further can include classifying the identified location as being a possible source of contaminated fuel and queries a database for additional data regarding the identified location.

In a fifty-fourth aspect, in addition to one or more of the preceding or following aspects, or in the alternative to some aspects, a method further can include determining sequences of refueling locations visited immediately before a sudden clogging curve begins.

In a fifty-fifth aspect, in addition to one or more of the preceding or following aspects, or in the alternative to some aspects, a method further can include evaluating one or more of weather data, temperature data, pressure data, humidity data, fuel filter model number, engine model number, driver ID, and detected refueling times to identify the effect of specific refueling locations on fuel filter loading.

In a fifty-sixth aspect, in addition to one or more of the preceding or following aspects, or in the alternative to some aspects, identifying refueling locations based on fuel level data and geolocation data includes identifying a geolocation at a time of a fuel level increase.

In a fifty-seventh aspect, in addition to one or more of the preceding or following aspects, or in the alternative to some aspects, a method further can include evaluating data from a water-in-fuel sensor and identifying an effect of specific refueling locations on water-in-fuel sensor data.

In a fifty-eighth aspect, in addition to one or more of the preceding or following aspects, or in the alternative to some aspects, a method further can include estimating remaining fuel filter life taking into account refueling locations used.

In a fifty-ninth aspect, a refueling guidance system for a vehicle is included having a system control circuit, wherein the system is configured to query a database that can include records of specific refueling locations and fuel filter loading rate data related to the specific refueling locations, wherein the system is configured to provide at least one of route and refueling site recommendations to an output device based on the fuel filter loading rate data.

In a sixtieth aspect, in addition to one or more of the preceding or following aspects, or in the alternative to some aspects, the system control circuit can further be configured to evaluate sensor data to determine changes in a filter restriction of a fuel filter, receive fuel level data, cross-reference geolocation data and fuel level data to identify refueling locations, correlate refueling locations with subsequent changes in filter restriction to identify an effect of specific refueling locations on fuel filter loading, and store data regarding the effect of specific refueling locations on fuel filter loading.

In a sixty-first aspect, in addition to one or more of the preceding or following aspects, or in the alternative to some aspects, the database is stored at a location remote from the system control circuit.

In a sixty-second aspect, in addition to one or more of the preceding or following aspects, or in the alternative to some aspects, the output device can include a user output device.

In a sixty-third aspect, in addition to one or more of the preceding or following aspects, or in the alternative to some aspects, the user output device can include a smart phone.

In a sixty-fourth aspect, in addition to one or more of the preceding or following aspects, or in the alternative to some aspects, the output device can include a vehicle navigation system.

In a sixty-fifth aspect, in addition to one or more of the preceding or following aspects, or in the alternative to some aspects, the output device can include a fleet management system.

In a sixty-sixth aspect, in addition to one or more of the preceding or following aspects, or in the alternative to some aspects, the system is configured to calculate a remaining distance to recommended fueling stations, compare the remaining distance to a remaining vehicle range based on a remaining fuel level, and alert a vehicle driver if they leave or are within a fixed distance of leaving the range of the recommended refueling stations.

In a sixty-seventh aspect, in addition to one or more of the preceding or following aspects, or in the alternative to some aspects, the system is further configured to query a database of filter providers, calculate a distance to the filter providers, compute a remaining useful life of a current fuel filter, and alert a vehicle driver if the remaining useful life of the current fuel filter is insufficient to reach at least one of the filter providers.

In a sixty-eighth aspect, in addition to one or more of the preceding or following aspects, or in the alternative to some aspects, the system is further configured to calculate an optimal location for a filter service vendor to meet a vehicle in need of fuel filter service based on the vehicle's planned route, minimizing the travel time of the service provider, and ensuring the filter is changed before it reaches the end of its useful life.

In a sixty-ninth aspect, a method of providing guidance for refueling a vehicle is included, the method including querying a database that can include records of specific refueling locations and fuel filter loading rate data related to the specific refueling locations and providing at least one of route and refueling site recommendations to an output device based on the fuel filter loading rate data.

In a seventieth aspect, in addition to one or more of the preceding or following aspects, or in the alternative to some aspects, further can include evaluating sensor data to determine changes in a filter restriction of a fuel filter, receiving fuel level data, cross-referencing geolocation data and fuel level data to identify refueling locations, correlating refueling locations with subsequent changes in filter restriction to identify an effect of specific refueling locations on fuel filter loading, and storing data regarding the effect of specific refueling locations on fuel filter loading.

In a seventy-first aspect, in addition to one or more of the preceding or following aspects, or in the alternative to some aspects, the method can further include calculating a remaining distance to recommended fueling stations, comparing the remaining distance to a remaining vehicle range based on a remaining fuel level, and alerting a vehicle driver if they leave or are within a fixed distance of leaving the range of the recommended refueling stations.

In a seventy-second aspect, in addition to one or more of the preceding or following aspects, or in the alternative to some aspects, the system is further configured to query a database of filter providers, calculate a distance to the filter providers, compute a remaining useful life of a current fuel filter, and alert a vehicle driver and/or a fleet manager or fleet management system if the remaining useful life of the current fuel filter is insufficient to reach at least one of the filter providers.

In a seventy-third aspect, in addition to one or more of the preceding or following aspects, or in the alternative to some aspects, the method can further include calculating an optimal location for a filter service vendor to meet a vehicle in need of fuel filter service based on the vehicle's planned route, minimizing the travel time of the service provider, and ensuring the filter is changed before it reaches the end of its useful life.

In a seventy-fourth aspect, in addition to one or more of the preceding or following aspects, or in the alternative to some aspects, the output device can include a user output device.

In a seventy-fifth aspect, in addition to one or more of the preceding or following aspects, or in the alternative to some aspects, the user output device can include a smart phone.

In a seventy-sixth aspect, in addition to one or more of the preceding or following aspects, or in the alternative to some aspects, the output device can include a vehicle navigation system.

In a seventy-seventh aspect, in addition to one or more of the preceding or following aspects, or in the alternative to some aspects, the output device can include a fleet management system.

In a seventy-eighth aspect, a service guidance system is included having a system control circuit, wherein the system is configured to calculate an optimal location for a filter service vendor to meet a vehicle in need of fuel filter service based on the vehicle's planned route, minimizing the travel time of the service provider, and ensuring the filter is changed before it reaches the end of its useful life.

In a seventy-ninth aspect, a method of providing guidance to a filter service vendor is included, the method including calculating a remaining range of a vehicle in need of fuel filter service, determining a projected location of the vehicle at or before the distance of the remaining range, and providing the projected location and/or a suggested route to reach the projected location to a filter service vendor.

In an eightieth aspect, a system for a vehicle is included having a fuel filter sensor device configured to generate data reflecting a filter restriction value of a fuel filter, a geolocation circuit configured to generate or receive geolocation data, wherein the system is configured to evaluate the fuel filter sensor data to determine changes in the filter restriction value, receive fuel level data, cross-reference geolocation data and fuel level data to identify refueling locations utilized, correlate refueling locations with subsequent changes in the filter restriction value to identify an effect of specific refueling locations utilized on fuel filter loading, and provide at least one of route and refueling site recommendations to a user output device based on the fuel filter loading rate data.

In an eighty-first aspect, in addition to one or more of the preceding or following aspects, or in the alternative to some aspects, the system is configured to query a database can include records of specific refueling locations and fuel filter loading rate data related to the specific refueling locations.

In an eighty-second aspect, a service guidance system is included having a system control circuit, wherein the system is configured to calculate an optimal route to a filter service vendor based on a vehicle's planned route, minimizing the travel time of the vehicle, and ensuring the filter is changed before it reaches the end of its useful life.

In an eighty-third aspect, a vehicle guidance system is included having a system control circuit, wherein the system is configured to calculate an optimal route to a destination taking into account a location of a filter service vendor, minimizing the travel time of the vehicle, and ensuring the filter is changed before it reaches the end of its useful life.

In an eighty-fourth aspect, in addition to one or more of the preceding or following aspects, or in the alternative to some aspects, the system is configured to optimize a preexisting planned route of the vehicle taking into account a location of a filter service vendor, minimizing the travel time of the vehicle, and ensuring the filter is changed before it reaches the end of its useful life.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
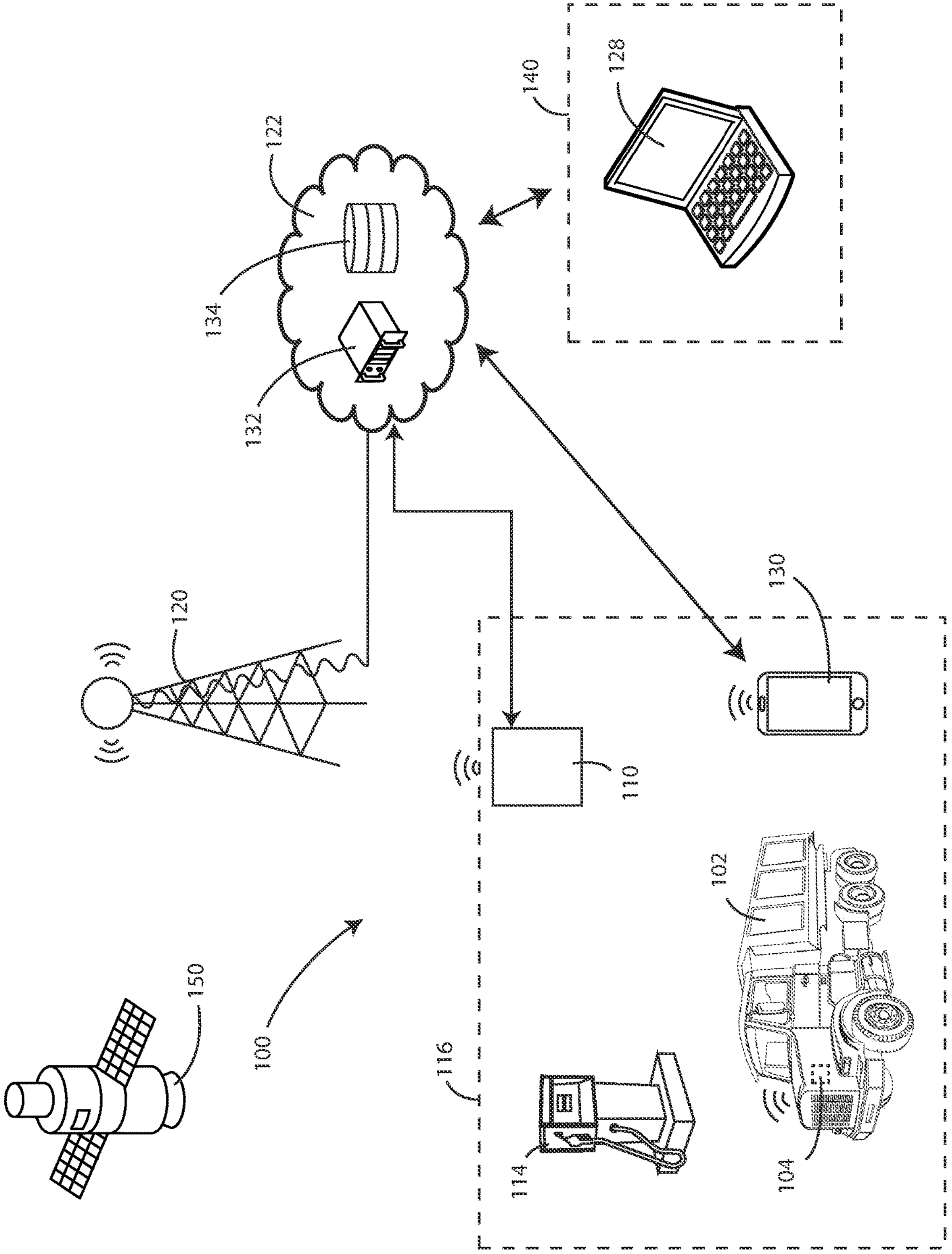
FIG. 1 is a schematic view of components of a fuel monitoring system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, fuel filters become saturated with impurities/contaminants during use in a process known as filter loading. As filter loading increases, filter restriction also increases until it reaches a level where the fuel filter needs to be replaced or otherwise serviced.

However, the level of impurities/contaminants/solids within fuel can vary based upon a wide range of factors which are present to differing degrees at specific refueling locations and all can contribute to abnormal filter loading and/or rapid plugging of the fuel filtration system. These factors include but are not limited to, hard particulate incursion from weather events, dirty hoses and pickups, rusting or otherwise degrading storage tanks, degraded hoses or valves, sediment stirred up by storage tank filling, salt carry over from the refining process, salt incursion in coastal areas, water incursion from weather events, leaks in underground storage tanks, tank washing, degraded biodiesel and biodiesel byproducts such as glycerin, glycerides, and sterols. In addition, temperature, moisture, oxygen levels, microbes and trace metals in the tank can all lead to rapid degradation of biodiesel. Further, the level of impurities/contaminants/solids with fuel can be impacted by biofilms and acid production associated with microbes, incompatibility of fuel additives in sequential fill ups such as acid additives with base additives, anionic with cationic salt additives, improperly blended polymeric fuel additives, and summer or winter fuel blends out of season, amongst others.

By monitoring filter loading behavior along with knowledge of refueling locations utilized it is possible to predict the effect of refueling at particular locations on filter loading. This can allow for the optimization of various aspects such as refueling locations utilized, routes taken, filtration system service location and timing, and fleet management, amongst others. This can also serve as the basis for a system to provide information on and/or make recommendations regarding various aspects such as when to refuel, which refueling location to use, which route to take, where to seek filtration system service, when to seek filtration system service, and other aspects related to vehicle operation and vehicle fleet management.

In various embodiments herein, a fuel monitoring system for a vehicle is included. The fuel monitoring system can include a fuel filter sensor device configured to generate and/or receive data reflecting filter restriction (including, but not limited to, a pressure drop across a fuel filter). The system can also include a geolocation circuit configured to generate and/or receive geolocation data. The system can also be configured to evaluate the pressure data to determine changes in the filter restriction, generate and/or receive fuel level data, cross-reference geolocation data and fuel level data to identify refueling locations, and correlate refueling locations with subsequent changes in fuel filter restriction to identify an effect of specific refueling locations on fuel filter loading.

In various embodiments herein, a refueling guidance system for a vehicle is included. The refueling guidance system can include a system control circuit and can be configured to query a database comprising records of specific refueling locations and fuel filter loading rate data related to the specific refueling locations. The system can also be configured to provide at least one of route and refueling location (site) recommendations based on the fuel filter loading rate data. For example, the system can be configured to provide any of the items determined herein and, specifically, at least one of route and refueling location (site) recommendations to an output device. In some embodiments, the output device comprising a user output device, such as a smart phone or the like. In some embodiments, the output device can be a vehicle navigation system. In some embodiments, the output device can be a fleet management system.

The term "vehicle" as used herein shall refer to any machine or device with an engine that moves and burns fuel and that must be refueled periodically.

Referring now to FIG. 1, a schematic view is shown of components of a fuel monitoring system 100 in accordance with various embodiments herein. FIG. 1 shows a fuel monitoring system 100 for a vehicle 102. The vehicle 102 includes a fuel filter system 104. In FIG. 1, the vehicle 102 is shown at a refueling location 116. The refueling location 116 also includes a fuel pump 114.

In some cases, the fuel filter system 104 can be capable of direct wireless data communication to the cloud 122 or to another data network. In some cases, the fuel filter system 104 can be capable of indirect wireless data communication to the cloud 122 or to another data network. In some embodiments, the fuel filter system 104 can communicate with a cell tower 120, which in turn can relay data communications back and forth with the cloud 122 and components thereof such as servers 132 (real or virtual) and databases 134 (real or virtual).

Wireless communication can take place using various protocols. For example, wireless communications/signals exchanged between the fuel monitoring system 100 or components thereof and the cloud 122 (or between components of the fuel monitoring system 100) can follow many different communication protocol standards and can be conducted through radiofrequency transmissions, inductively, magnetically, optically, or even through a wired connection in some embodiments. In some embodiments herein, IEEE 802.11 (e.g., WIFI®), BLUETOOTH® (e.g., BLE, BLUETOOTH® 4.2 or 5.0), ZIGBEE®, or a cellular transmission protocol/platform can be used such as CDMA, cdmaOne, CDMA2000, TDMA, GSM, IS-95, LTE, 5G, GPRS, EV-DO, EDGE, UMTS, HSDPA, HSUPA, HSPA+, TD-SCDMA, WIMAX, and the like. In various embodiments, a different standard or proprietary wireless communication protocol can also be used.

As referenced, cloud 122 resources may include databases 134. Such databases 134 can store various pieces of information including, but not limited to, refueling location data (such as refueling location IDs, refueling location geolocation data, fuel filter loading rate data related to specific refueling locations, refueling location estimated impurity/contamination information, refueling location visit data, refueling location filter loading impact data, and the like), fleet data, vehicle data, filtration system data, and the like.

It will be appreciated that database content may be spread across many different physical systems, devices, and locations. Further, while not depicted in FIG. 1, it will be appreciated that database records can also be stored at the level of the fuel filter system 104 itself. In various embodiments, the database 134 or portions thereof can be stored at a location remote from other components of the system, such as the fuel filter system 104. In some embodiments, records or portions of the database can be stored across different physical locations and, in some embodiments, cached across different physical locations for ready access.

In some embodiments, the refueling location 116 can include a location communication device 110. The location communication device 110 can include various components. In some embodiments, the location communication device 110 can be a wireless data gateway, including components such as a router and/or other data networking hardware. In some cases, the fuel filter system 104 can be in wireless communication with the location communication device 110 in order to provide communication with the cloud 122 or another data network. In some cases, the fuel filter system 104 can receive information from the location communication device 110 such as geolocation data (which can include latitude/longitude coordinates amongst other things), or other location identifying information such as a nearest address, nearest landmark, etc. As used herein, the term "geolocation data" shall include reference to all location identifying data, unless the context dictates otherwise.

In some cases, geolocation data can be derived from a satellite 150 based geolocation system. Such systems can include, but are not limited to, GPS L1/L2, GLONASS G1/G2, BeiDou B1/B2, Galileo E1/E5b, SBAS, or the like. In various embodiments, the system can include a geolocation circuit (described below) that can include appropriate signal receivers or transceivers to interface with a satellite 150 and/or the geolocation circuit can interface with and/or receive data from a separate device or system that provides geolocation data or derives geolocation data from a satellite 150 or other device. However, it will be appreciated that geolocation data herein is not limited to just that which can be received from or derived from interface with a satellite 150. Geolocation data can also be derived from addresses, beacons, landmarks, various referential techniques, IP address evaluation, and the like.

In various embodiments, the fuel monitoring system for a vehicle 102 can also include and/or can be in communication with a mobile communications/guidance device 130. In some cases, the mobile communications/guidance device 130 can be used to provide data communication for the fuel filter system 104 and the cloud or another data network. In various embodiments, the mobile communications/guidance device 130 can provide outputs to or inputs from the vehicle 102 or a driver of the vehicle 102. In some cases, the mobile communications device can be used to provide recommendations (visually, audibly, and/or haptically) to the driver of the vehicle. For example, in various embodiments, a recommendation can be generated by the system and can be forwarded to a mobile communications/guidance device 130 associated with a vehicle 102 or a driver of a vehicle 102.

Specific recommendations/reports generated by the system can include specific points of information. However, as merely one example, the fuel monitoring system 100 and/or components thereof can be configured to generate a report relating to different fueling locations (and/or patterns of the same) and the impact of such locations on filter loading rates and/or recommendations regarding fueling locations based on filter loading rates. As another specific example, the fuel monitoring system 100 and/or components thereof can be configured to generate a report that profiles the frequency with which different drivers in a fleet use recommended and dis-recommended fueling stations.

In some embodiments the mobile communications/guidance device 130 can be, for example, a smart phone, or another type of computing device including wireless communication capabilities. In some embodiments the mobile communications/guidance device 130 can be a vehicle navigation system.

In some embodiments, the fuel monitoring system 100 can also include and/or be in communication with a fleet monitoring center 140 (real or virtual). The fleet monitoring center 140 can include a remote computing device 128 and can receive information and/or recommendation about specific vehicles and/or specific refueling locations. In some cases, the fuel monitoring system 100 can be used to provide recommendations to a fleet control operator at the fleet monitoring center 140 and/or receive information or instructions from a fleet control operator at the fleet monitoring center 140.

In various embodiments, systems described herein can also serve as, or function as, or be a refueling guidance system for a vehicle 102. For example, the system 100 can be configured to query a database 134 that can include records of specific refueling locations and fuel filter loading rate data related to the specific refueling locations. The system 100 can be configured to provide at least one of route and refueling site recommendations to an output device based on the fuel filter loading rate data. In some embodiments, the output device comprising a user output device, such as a smart phone or the like. In some embodiments, the output device can be a vehicle navigation system. In some embodiments, the output device can be a fleet management system.

Figure 2:
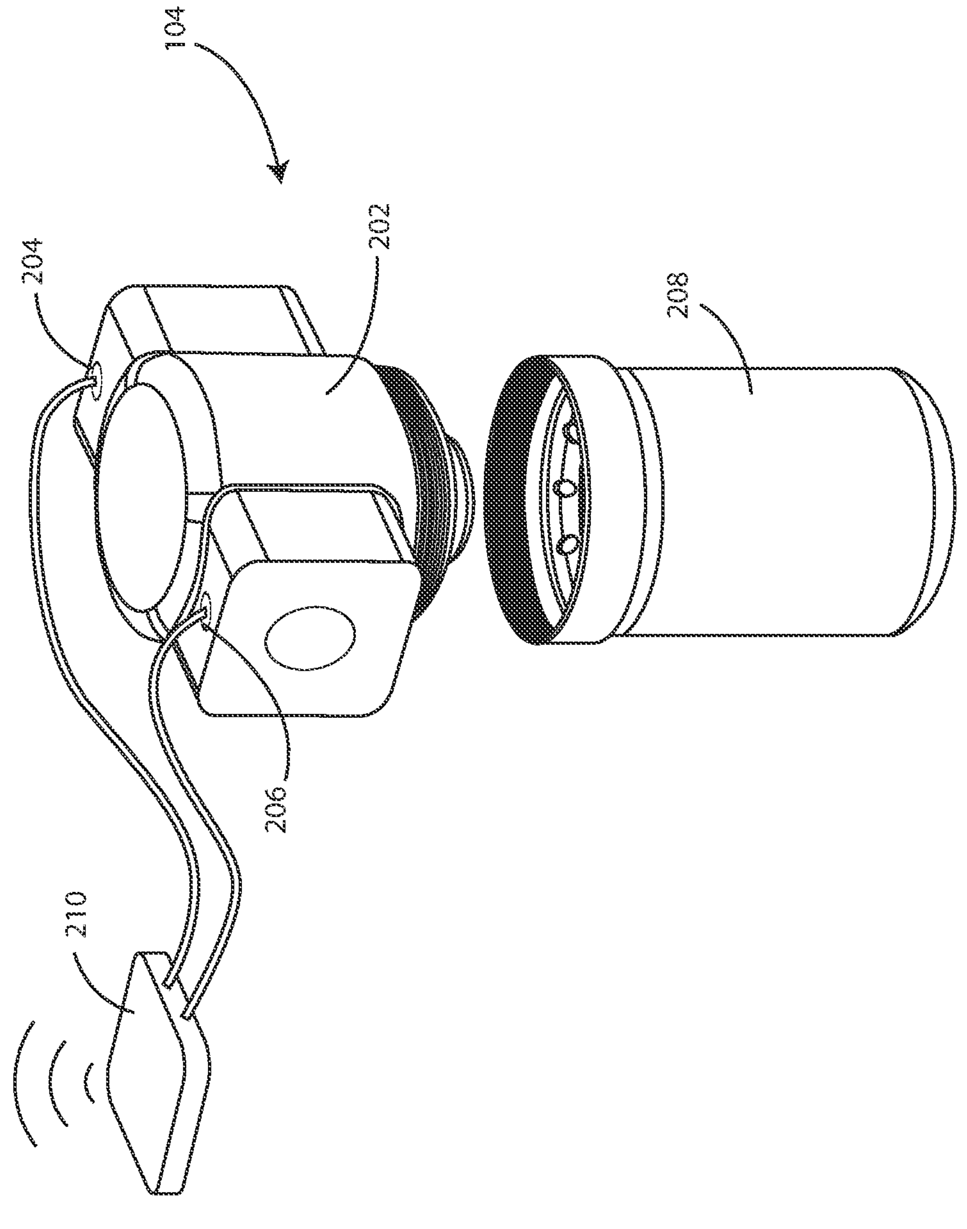
FIG. 2 is a schematic view of fuel filtering device and components of a fuel monitoring system in accordance with various embodiments herein.

Referring now to FIG. 2, a schematic view is shown of components of a fuel monitoring system in accordance with various embodiments herein. In specific, a fuel filter system 104 is shown. The fuel filter system 104 includes a filter head unit 202 or housing. The fuel filter system 104 also includes a fuel filter 208. In some cases, the fuel filter 208 can be a spin-on type of fuel filter. However, other types of fuel filters are also contemplated herein.

The fuel filter system 104 can include one or more sensor device(s) and/or can be configured to receive data from one or more sensor device(s). For example, the fuel filter system 104 can include an upstream pressure sensor 204 and a downstream pressure sensor 206. In some embodiments, the upstream pressure sensor 204 and the downstream pressure sensor 206 can both be in fluid communication with the fuel line or can otherwise be configured to sense a pressure within the fuel line. In specific, the fuel filter sensor device can include an upstream pressure sensor 204 configured to sense a pressure in a fuel line upstream of the fuel filter 208 and a downstream pressure sensor 206 configured to sense a pressure in the fuel line downstream of the fuel filter 208. Based on pressure data/signals generated by the upstream pressure sensor 204 and the downstream pressure sensor 206, a pressure-drop ("delta P") across the fuel filter 208 can be calculated. Pressure data/signals can also include or otherwise be paired with time stamps and can be stored by various components of the system. It will be appreciated, however, that in various embodiments other measures of filter restriction (pressure based or otherwise) can be sensed or otherwise calculated. In some embodiments, only a single pressure sensor (upstream or downstream of the fuel filter) is used either alone or in combination with other types of sensors. In still other embodiments, a different number of pressure sensors can be used.

The fuel filter system 104 can include a fuel filter monitoring device 210. The fuel filter monitoring device 210 can receive data/signals from various sensors (fuel filter sensor devices) including, but not limited to, upstream pressure sensor 204 and downstream pressure sensor 206. The fuel filter monitoring device 210 can perform various functions including, but not limited to, calculating filter restriction, calculating pressure drop, filtering data, processing data, compressing data, storing data, transmitting data, and executing various operations described herein. In some embodiments, the fuel filter monitoring device 210 can exchange wireless and/or wired data transmissions with other devices. In some embodiments, the fuel filter monitoring device 210 can be directly or indirectly in communication with the cloud or another data network.

While certain types of pressure sensors are demonstrated herein as specific examples of fuel filter sensor devices that can be configured to generate data reflecting a filter restriction value of a fuel filter, it will be appreciated that various other types of sensors can also serve as fuel filter sensor devices. By way of example, sensors for filter restriction values can include differential pressure sensors, non-differential pressure sensors, acoustic sensors, optical sensors, electromagnetic sensors, fuel efficiency sensors, engine operation sensors, fuel pump sensors (including, but not limited to sensors responsive to the amount of energy consumed in operating a fuel pump, such as by an electric motor driving the same), and the like. Further, it will be appreciated that in some cases herein fuel filter sensors herein can function as an interface receiving data reflecting filter restriction values from another device or system.

It will be appreciated that it can be efficient to rely upon data generated by other devices/systems when available. For example, CANBus refers to a vehicle data bus standard designed to allow devices and electronic control units to communicate with one another. Many vehicles include a CANBus network and communication with the CANBus network can provide many different types of data. For example, interfacing with the CANBus network can provide one or more of fuel level data, various types of engine data (including, but not limited to, engine RPM data, engine hours of operation data, odometer data, engine/vehicle temperature data), ambient temperature data, geolocation data, and the like.

Figure 3:
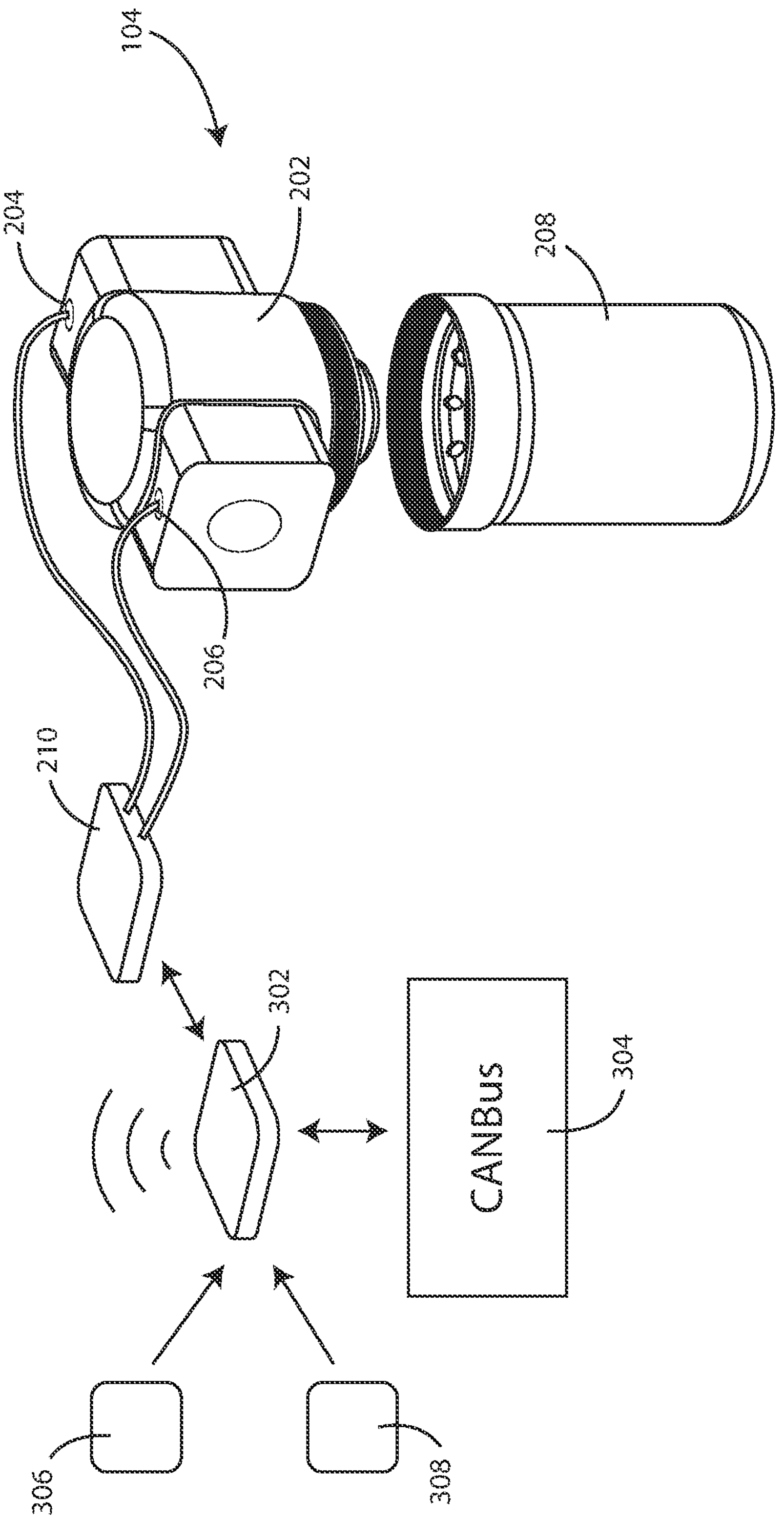
FIG. 3 is a schematic view of fuel filtering device and components of a fuel monitoring system in accordance with various embodiments herein.

Referring now to FIG. 3, a schematic view is shown of components of a fuel monitoring system in accordance with various embodiments herein. FIG. 3 is generally similar to FIG. 2, but it also includes additional features that can be part of various embodiments herein. As before, a fuel filter system 104 is shown including a filter head unit 202 and a fuel filter 208. The fuel filter system 104 can include one or more sensor device(s) and/or can be configured to receive data from one or more sensor device(s). For example, the fuel filter system 104 can include an upstream pressure sensor 204 and a downstream pressure sensor 206.

The fuel filter system 104 can also include a fuel filter monitoring device 210. In this example, the fuel filter monitoring device 210 can also interface with a separate device 302. The separate device 302 can serve as a gateway and/or a source or aggregator of data related to the vehicle. In some embodiments, the separate device 302 can generate its own data, such as geolocation data. In some cases, the separate device 302 can provide communication with a CANBus network 304. In various embodiments, fuel level data can be received from a CANBus network 304 and conveyed to components of the system herein through the separate device 302.

It will be appreciated that the separate device 302 can interface with many different sources of data. Figuratively, the separate device 302 can be in communication with a first additional data generating or receiving device 306 and/or a second additional data generating or receiving device 308. Data can include, but are not limited to, one or more of weather data, temperature data, pressure data, humidity data, fuel filter model number, engine model number, driver ID, and detected refueling times.

In some specific examples, a water-in-fuel sensor can specifically be included. For example, the first or second additional data generating and/or receiving device can include or can be in communication with a water-in-fuel sensor. In various embodiments, water can serve as an example of a particular type of fuel contaminant. In various embodiments herein, the system can correlate refueling locations with subsequent changes in the data from a water-in-fuel sensor to identify an effect of specific refueling locations on water-in-fuel sensor data (and therefore on the amount of water in the fuel).

Various water-in-fuel sensors can be used. In some embodiments, water-in-fuel sensors herein can include optical water-in-fuel sensors. In some embodiments, an exemplary optical water-in-fuel sensor can include a light emitter (such as an LED or other emitter) and a light detector (such as a photodiode, phototransistor, photoresistor, CMOS sensor, a charge-coupled device, or the like). The light emitter can be configured to emit light into a sample of fuel and the light detector can be configured to receive light that has passed through the sample. For example, the light emitter and light detector can be arranged on opposing sides of a channel through which fuel flows. The absorbance of water at certain wavelengths of light (including, but not limited to, near infrared light or light centered at a wavelength of about 1550 nanometers) is different than that of fuel. Therefore, a signal from the light detector will vary based upon the amount of water in the fuel. In some embodiments, fuel to be evaluated (such fuel flowing within a fuel line) can be at least partially diverted to pass through a sensor channel (such as a microfluidic channel) with a light emitter that emits light into the sensor channel and the light detector that receives light from the sensor channel. The signal from the light detector can then be evaluated to determine the amount of water in the fuel passing through the sensor channel. Similar optical sensors can also be used to identify other possible contaminants. Exemplary water-in-fuel sensors can include those described in Publ. PCT Appl. No. PCT/US2019/034809, published as WO2019/232305 and titles "DROPLET SENSORS FOR FUEL SYSTEMS", the content of which is herein incorporated by reference in its entirety. It will be appreciated that data from water-in-fuel sensors can be used in isolation or in combination with other types of contaminant data or restriction data discussed herein.

In some specific examples, other types of contaminant sensors can also be included. For example, the first or second additional data generating and/or receiving device can include or can be in communication with another type of fuel contaminant sensor. In various embodiments herein, the system can then correlate refueling locations with subsequent changes in the contaminant levels as identified (at least partially) by a contaminant sensor to identify an effect of specific refueling locations on contaminant levels and therefore on the amount of contaminants in the fuel. Such contaminant sensors can include, but are not limited to, on-vehicle particulate counters/monitors. In some embodiments, the contaminant sensor can include an optical-based sensor that uses detection of light blocking for particle detection. For example, particles can pass through an optical flow cell including a lighter emitter. The particles can block portions of the light, creating a shadow. These shadows can be detected by a light detector. Contaminant sensors can also rely upon other methods of detection other than light based optical systems. For example, contaminant sensors can also rely upon electrical, magnetic, weight, and/or density properties in order to detect contaminants. In some embodiments, a contaminant sensor herein can detect particles in accordance with ISO 11171 regarding particle count data in fluids. It will be appreciated that data from other types of contaminant sensors (and specifically data from particulate counters/monitors) can be used in isolation or in combination with other types of contaminant data or restriction data discussed herein.

In various embodiments herein, the system can evaluate the pressure data to determine changes in filter restriction, receive fuel level data, cross-reference geolocation data and fuel level data to identify refueling locations, and correlate refueling locations with subsequent changes in fuel filter restriction to identify an effect of specific refueling locations on fuel filter loading behavior.

Figure 4:
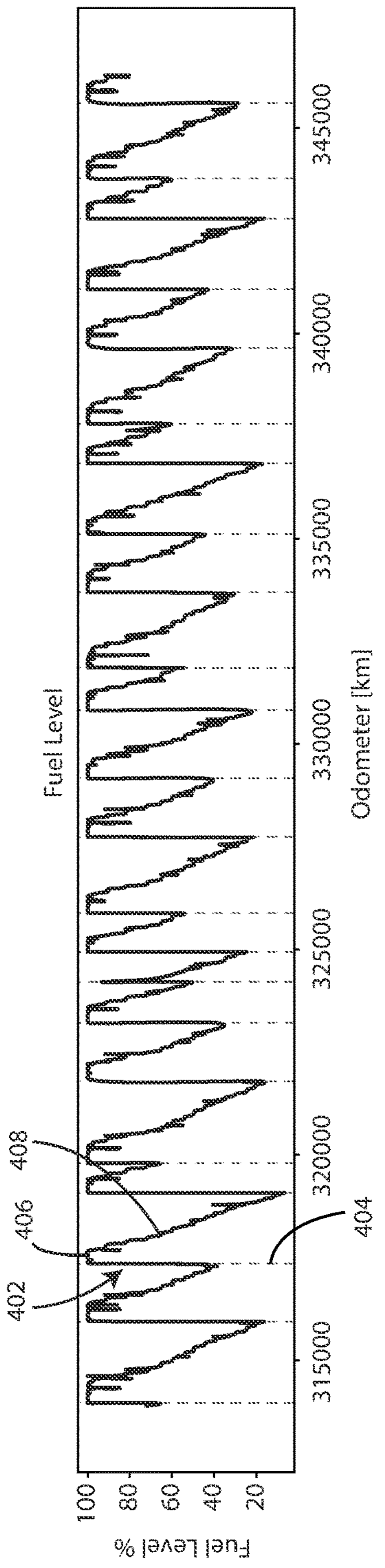
FIG. 4 is a graph of fuel level of a vehicle over distance driven in accordance with various embodiments herein.

Referring now to FIG. 4, a graph of fuel level of a vehicle 102 over distance driven is shown in accordance with various embodiments herein. As can be seen, the graph is characterized by a set of repeating features including idling times 406, time spent under load 408, and refueling events 404. In particular, FIG. 4 shows a sudden fuel level volume increase 402 which can be interpreted as a refueling event 404.

Figure 5:
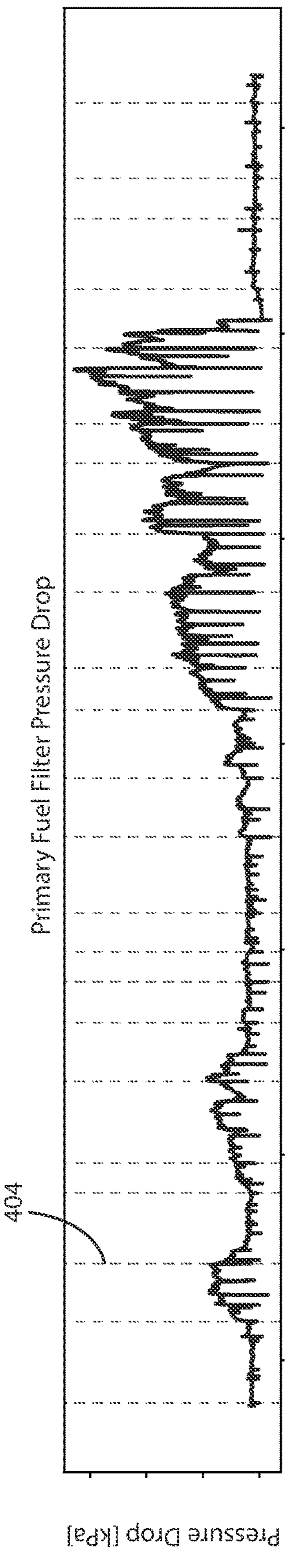
FIG. 5 is a graph of fuel filter pressure drop over distance driven in accordance with various embodiments herein.

Referring now to FIG. 5, a graph of fuel filter 208 pressure drop over distance driven is shown in accordance with various embodiments herein. The timing/odometer readings of FIGS. 4 and 5 are synchronized such that FIG. 5 also shows refueling events 404 and, more specifically, the same refueling events as shown in FIG. 4. Therefore, the impact of a particular refueling event on subsequent filter loading can be precisely identified and evaluated.

Further, cross-referencing geolocation data and fuel level data can be used to identify refueling locations including, specifically, identifying a geolocation at a time of a fuel level increase. Cross-referencing geolocation data and fuel level data can include various possible operations. In some embodiments, both fuel level data and geolocation data can be time stamped or otherwise associated with time such that the two types of data can be synchronized with respect to time. Then, when a fuel level increase of a sufficient magnitude is detected, the synchronous geolocation data can be identified.

In some cases, specific refueling locations can be identified just by their geolocation data, such as by longitude and latitude coordinates. However, in other embodiments, synchronous geolocation data can then be compared to locations of known refueling locations for various purposes, such as to confirm that a refueling event has occurred and/or to provide additional data to be used by the system for various purposes including in generating recommendations. For example, coordinates can be sent through a data network to a location API such as the "Places API" commercially available as part of the Google Maps Platform in order to identify whether a known fueling station exists at or near a particular set of coordinates. Similarly, the synchronous geolocation data can be subjected to a reverse geocoding procedure in order to convert coordinates (for example) into an address. For example, coordinates can be sent through a data network to an API such as the "Geocoding API" commercially available as part of the Google Maps Platform. The discovered address can then be stored and/or can be matched up against the addresses of known refueling locations in a database for various purposes, such as to confirm that a refueling event has occurred and/or to provide additional data to be used by the system for various purposes including in generating recommendations and/or alerts.

The magnitude of fuel level increases sufficient to infer that a refueling event has taken place can vary. In some embodiments, the system can infer that a refueling event has taken place if the fuel level increases by an amount crossing a threshold value. For example, a fuel level increase of at least 5, 10, 20, 30, 40, 50, 60, 70, 80, or 90 percent (as a percentage of the total fuel capacity of the vehicle), or an amount falling within a range between any of the foregoing, can be used as a threshold value. In various embodiments, the system can require that such an increase must be preserved for a predetermined length of time in order for a refueling event to be inferred in order to avoid the adverse effects of spurious fuel level sensor data. In various embodiments, the system can require that such an increase must represent an average value over a plurality of fuel level data readings.

In some embodiments, the system can send a query to a vehicle driver and/or a fleet controller in order to confirm that a refueling event has just taken place. For example, the system can present a query to a driver through a mobile communications/guidance device 130 or another device after a possible refueling event has been detected and then receive input back in order to confirm the same.

In some embodiments, the system can query the vehicle driver and/or receive input from the vehicle driver for purposes other than just confirmation. For example, the vehicle driver can provide input to the system that a refueling event has take place. The vehicle driver can provide such input in response to a query from the system and/or can simply provide such input unsolicited by the system.

Figure 6:
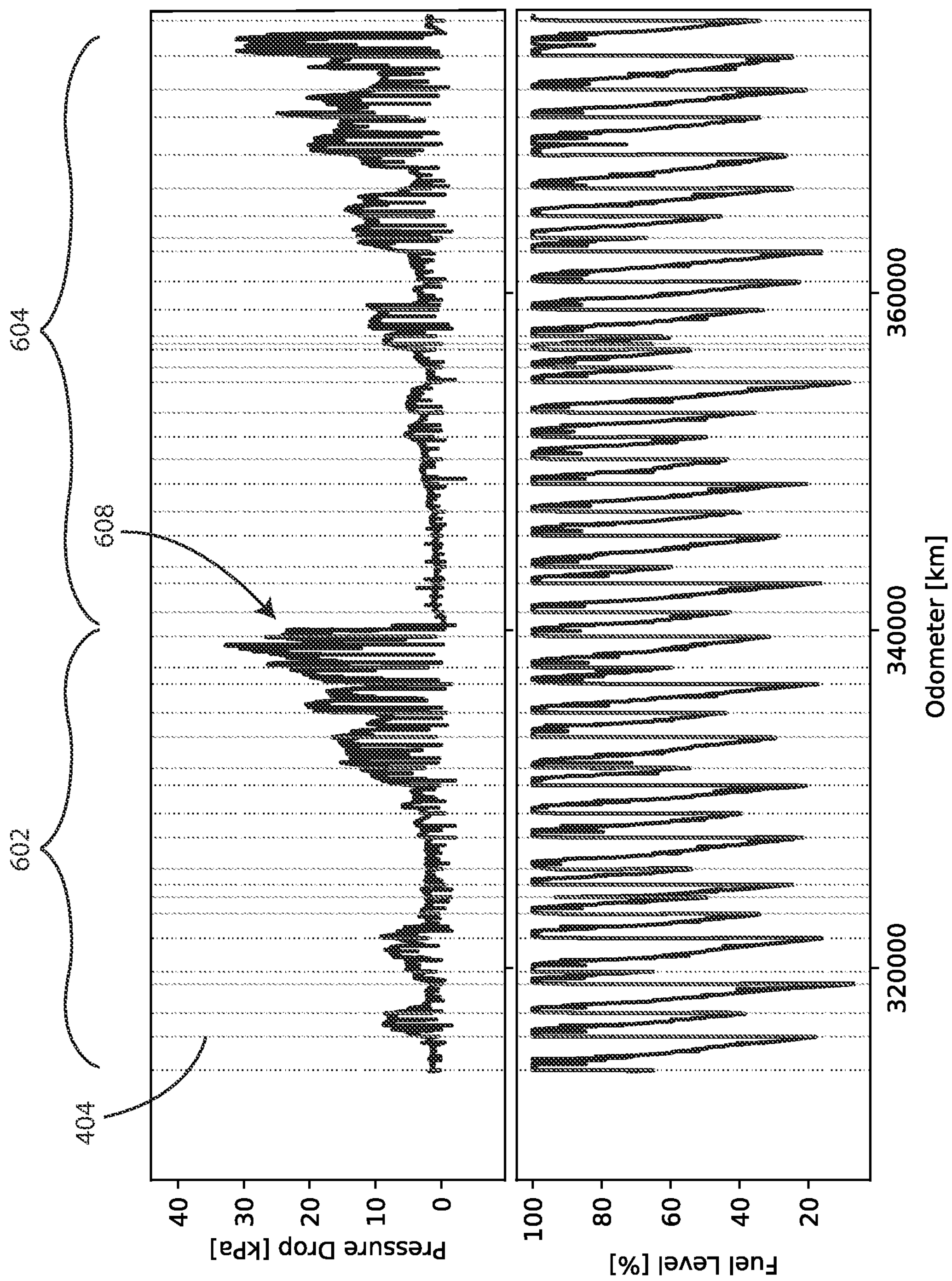
FIG. 6 is a graph of fuel filter pressure drop and fuel level of a vehicle over distance driven for two fuel filters through changeout.

It will be appreciated that fuel filter restriction (including, but not limited to, pressure drop) and fuel level information can be monitored over multiple fuel filter lifetimes. For example, referring now to FIG. 6, a graph is shown of fuel filter 208 pressure drop and fuel level of a vehicle 102 over a distance driven spanning two fuel filters through change-out. FIG. 6 shows refueling events 404 along with a first filter lifetime 602 and a second filter lifetime 604. FIG. 6 shows a fuel filter change event 608.

A fuel filter change event 608 can be determined or inferred based on observing a sudden reduction in pressure drop across the filter (or other measure of fuel filter restriction) and, specifically, a reduction down to nominal pressure drop levels for a new fuel filter (or within a range of pressure drop levels for a new filter). In some embodiments, a fuel filter change event can be inferred by sensing a fuel filter restriction that goes downward by at least a threshold value. For example, the threshold can be at least about a 5, 10, 20, 30, 40, 50, 60, 70, 80, or 90 percent reduction in sensed filter restriction in order to infer that a new fuel filter has been installed. Because the vehicle engine will generally be shut down during fuel filter servicing, in some embodiments herein the threshold filter restriction can be evaluated from the time an engine is shut down to the next time it is started up.

It will be appreciated that total costs of operating a vehicle include various aspects beyond just fuel costs. For example, maintenance service and replacement part costs can be significant. Since fuel filters must be periodically replaced, their cost along with the cost of service associated with replacing the fuel filter can also be included with the total costs of operating a vehicle. However, since different refueling locations can impact filter loading behavior differently (and thus can impact the useful life of a fuel filter), different refueling locations may have different effective total costs. Thus, knowledge of the total cost associated with a particular refueling location beyond the posted price of fuel per gallon can be used in forming a recommendation of which refueling location to use.

Figure 7:
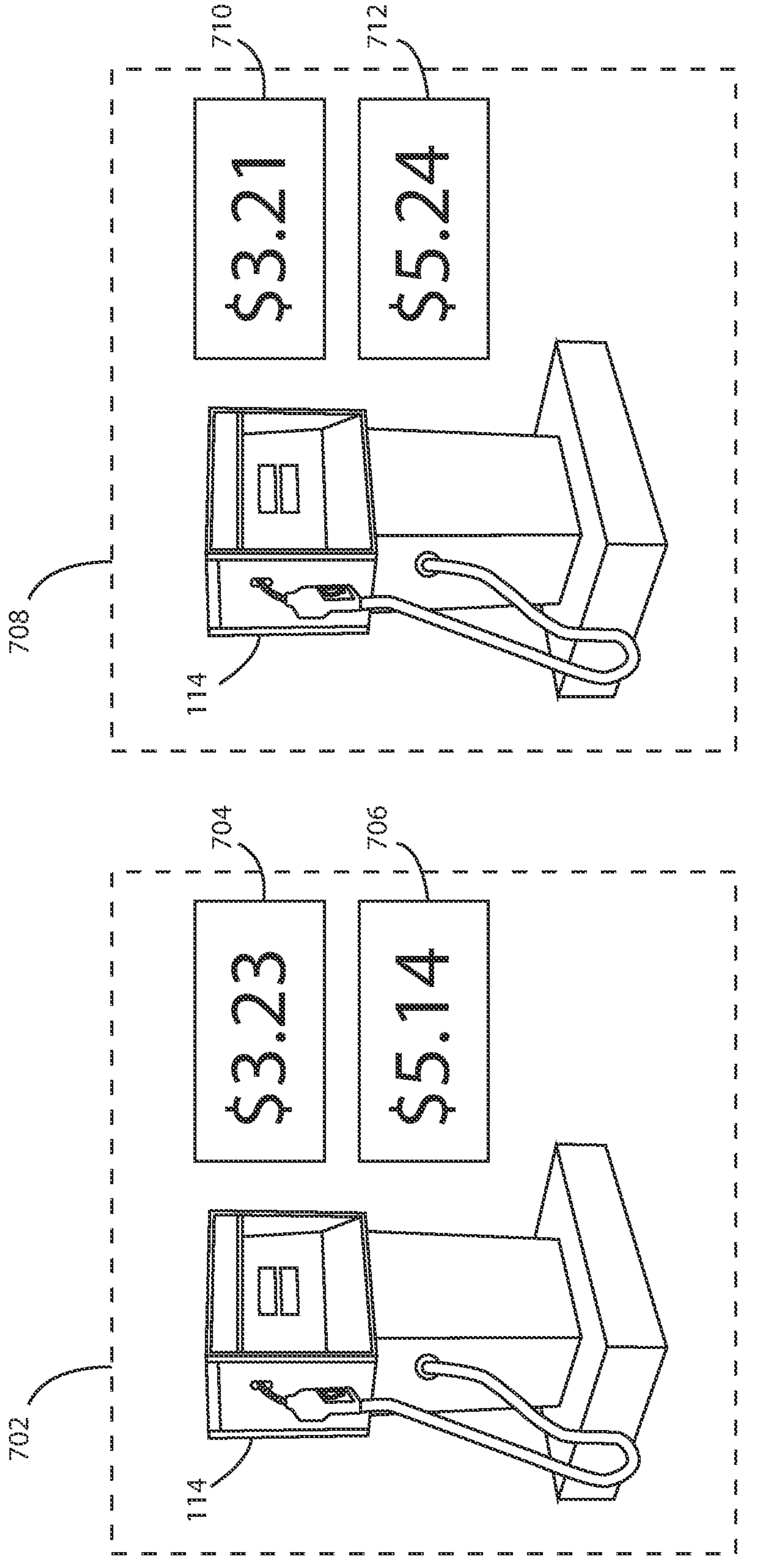
FIG. 7 is a schematic diagram illustrating fueling location costs in accordance with various embodiments herein.

Referring now to FIG. 7, a schematic diagram illustrating fueling location costs is shown in accordance with various embodiments herein. A first possible refueling location 702 has a first nominal fuel cost 704. The first possible refueling location 702 also includes a first total cost 706. A second possible refueling location 708 has a second nominal fuel cost 710. The second possible refueling location 708 also includes a second total cost 712.

The total costs 706, 712 can be calculated or estimated in various ways. In various embodiments, the system can be configured to calculate a cost associated with a particular refueling location 116 at least partially based on estimated expected fuel filter 208 loading rate. This can be performed in various ways. In one approach, the impact of a particular refueling location on fuel filter loading can be used to calculate how quickly the current fuel filter at the current filter restriction level will become loaded sufficiently to hit a terminal or end-of-life state. For example, the system can calculate how quickly the current fuel filter is likely to reach a pressure drop of 35 to 40 kPa (assuming the fuel filter is a primary fuel filter). In some embodiments, this calculation can be performed by first identifying filter loading curves from past visits to a particular refueling location (which can be based on past visits of the particular vehicle to the particular refueling location, past visits of other vehicles within a fleet to the particular refueling location, and/or past visits of third-party vehicles to the particular refueling location) and/or an average or other statistical treatment of the same. With a loading curve in hand along with a current filter restriction value of the current filter, then an estimate of distance remaining before a terminal or end-of-life state is reached can be calculated. Then, using the cost of fuel filter service and parts, an amount of cost attributable to the fuel filter as a result of a particular refueling location can be derived. In some cases, the amount of cost attributable to the fuel filter as a result of a particular refueling location can be compared with an average value for all refueling locations, an average value for all refueling locations within a particular region, or an average value for all refueling locations at a particular stop or exit of a route, to result in a comparative cost and/or to serve as a basis for a recommendation.

In various embodiments, the system can be further configured to generate a recommendation including a recommended refueling location. In some cases, a recommendation can be the result of a comparison of the filter loading curves from a set of different refueling locations, with the refueling location having the flattest or most slowing rising filter loading curve being the recommended refueling location. The set of different refueling locations for consideration can be selected in various ways. For example, the set can be all or some refueling locations at a particular stop or exit along a route, all or some refueling locations along a particular route, all refueling locations that are approved by fleet management, all refueling locations that are within a certain distance of the current location of the vehicle (such as in the same direction of the route being taken by the vehicle), or the like.

In some cases, analysis of the impact of refueling locations on fuel filter loading phenomena can include an evaluation of a sequence of refueling locations utilized. Different geographic regions may have slightly different fuel formations and/or additives. In some cases, components within fuel from one location may interact with components within fuel from another location in a manner sufficient to impact the fuel filter loading behavior. Thus, while an adverse impact on fuel filter loading occur immediately after a particular fueling location has been utilized, the effect may be a result not just of the immediate fueling location, but a function of the sequence of fueling locations utilized.

Figure 8:
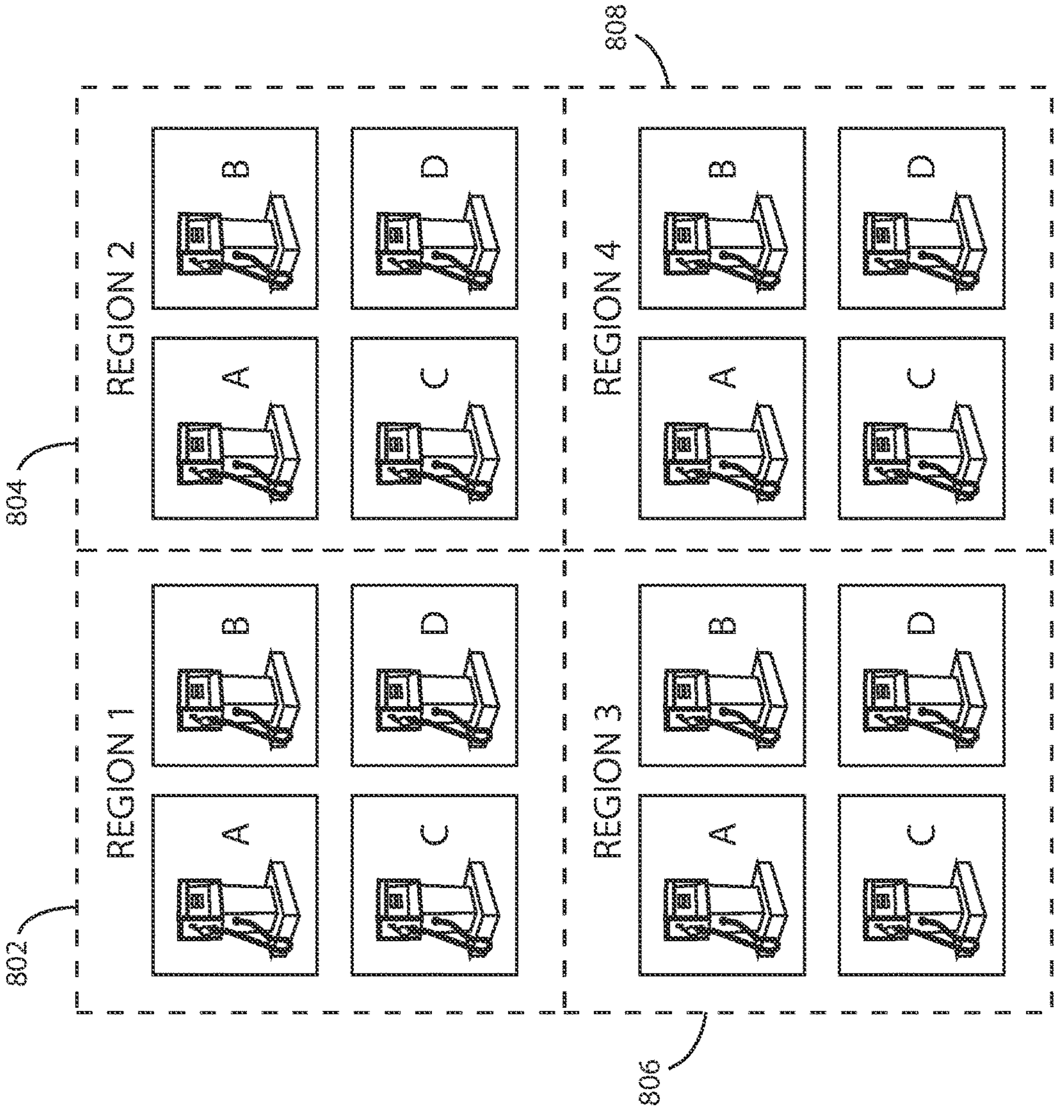
FIG. 8 is a schematic diagram illustrating fueling locations within different regions in accordance with various embodiments herein.
Figure 9:
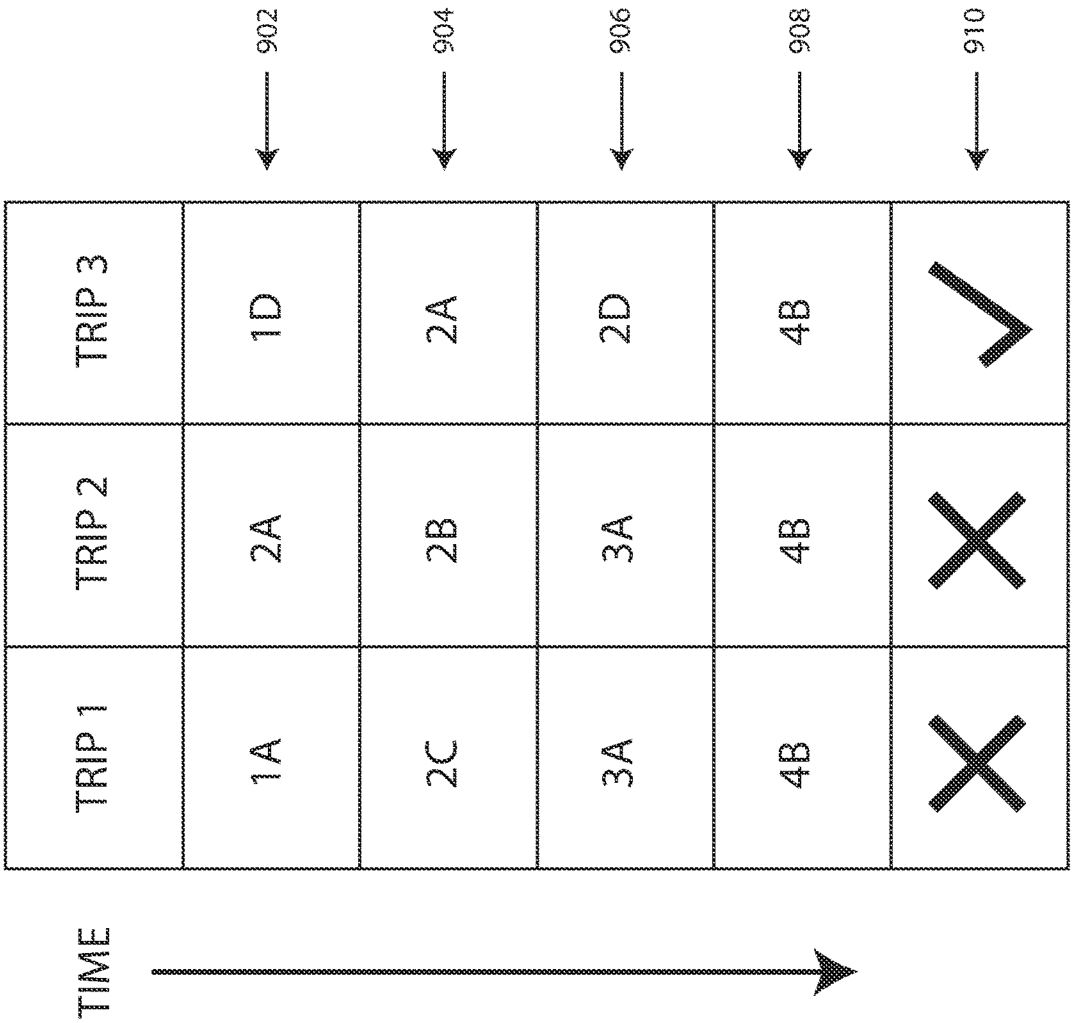
FIG. 9 is a schematic diagram illustrating sequences of fueling location visits for multiple trips in accordance with various embodiments herein.

For example, referring now to FIG. 8, a schematic diagram illustrating fueling locations within different regions is shown in accordance with various embodiments herein. Regions (which could be states, counties, or the like) can include a first region 802, a second region 804, a third region 806, and a fourth region 808. Each of the regions can include a plurality of individual refueling locations disposed therein (A-D). Referring now to FIG. 9, a schematic diagram is shown illustrating sequences of refueling location visits for multiple trips/itineraries in accordance with various embodiments herein. For each of the refueling location visits, FIG. 9 shows a refueling location identifier. For example, the first refueling location 902 for trip 1 is "1A". The second refueling location 904 for trip 1 is "2C". The third refueling location 906 for trip 1 is "3A" and the fourth refueling location 908 for trip 1 is "4B". FIG. 9 also shows a fuel system status 910 that reflects, for example, a status of a fuel filtration system of a vehicle at the end of the trip. In this example, both trip 1 and trip 2 end with a negative status while trip 3 ends with a positive status. In some cases, a negative status can reflect an abnormal filter loading pattern while a positive status reflects a normal filter loading pattern.

FIG. 9 illustrates the scenario where a pattern of refueling location visits can allow for a better understanding of scenarios leading to abnormal fuel filter loading. For example, both trip 1 and trip 2 include a last stop at location "4B" and result in a negative status. As such, evaluating trip 1 and trip 2 in isolation may lead to a conclusion that location "4B" is the source of fuel having an adverse impact on fuel filter loading. However, by also evaluating trip 1, which also has location "4B" as the last stop, but does not have location "3A" as the penultimate stop and which did not result in a negative status, it becomes clear that the problematic scenario is more precisely characterized as refueling a location "3A" followed by location "4B". By determining such insights, systems herein can provide recommendations that take into account the pattern of refueling locations that have been visited. For example, systems herein can provide recommendations including the optimal refueling location to utilize as part of a sequence of refueling locations. Also, systems herein can provide recommendations including a sequence of optimal refueling locations to utilize.

Systems herein can also provide route recommendations, including those that optimize refueling locations utilized in view of other parameters including one or more of distance traveled, time required for travel (speed), availability of maintenance sites along the route, and the like. This can be performed in various ways. As merely one example, based on a given starting point and a destination, possible routes can be identified using various techniques including utilizing an API such as the "Directions API" commercially available as part of the Google Maps Platform. Further, based on a given starting point, a destination, and a waypoint such as particular refueling location or filter service provider location, optimized routes can be identified using various techniques including utilizing an API such as the "Directions API" commercially available as part of the Google Maps Platform.

In various embodiments, for each route, zones of likely refueling stops ("refueling zones") can be calculated taking into account the current fuel level of the vehicle and an estimate of fuel mileage. For example, an estimated end-of-fuel point can be determined and then all refueling locations along a given route up to a fixed distance prior to the end-of-fuel point can be evaluated. The best refueling location, or an average of the top refueling locations, can then be used as an assumption for the refueling location that will be utilized within a given refueling zone and then effects on expected fuel filter loading can be calculated using data stored regarding the impact of such refueling locations on filter loading curves. This can be done across all refueling zones associated with a particular route initially identified as being a possible route. In so doing, the optimal route from the perspective of fuel filter loading can be identified. However, other factors can also be included/considered when calculating the optimal route including, but not limited to, distance travelled, time required for travel (speed), weather, availability of maintenance sites, availability of parts, price of fuel at refueling locations along the route, etc.

In various embodiments, a refueling guidance system for a vehicle 102 can include a system control circuit and can be configured to query a database including records of specific refueling locations and fuel filter loading rate data related to the specific refueling locations, wherein the system can be configured to provide at least one of route and refueling site recommendations to a mobile communications/guidance device 130 and/or a user output device based on the fuel filter loading rate data. In some embodiments, the output device comprising a user output device, such as a smart phone or the like. In some embodiments, the output device can be a vehicle navigation system. In some embodiments, the output device can be a fleet management system.

Figure 10:
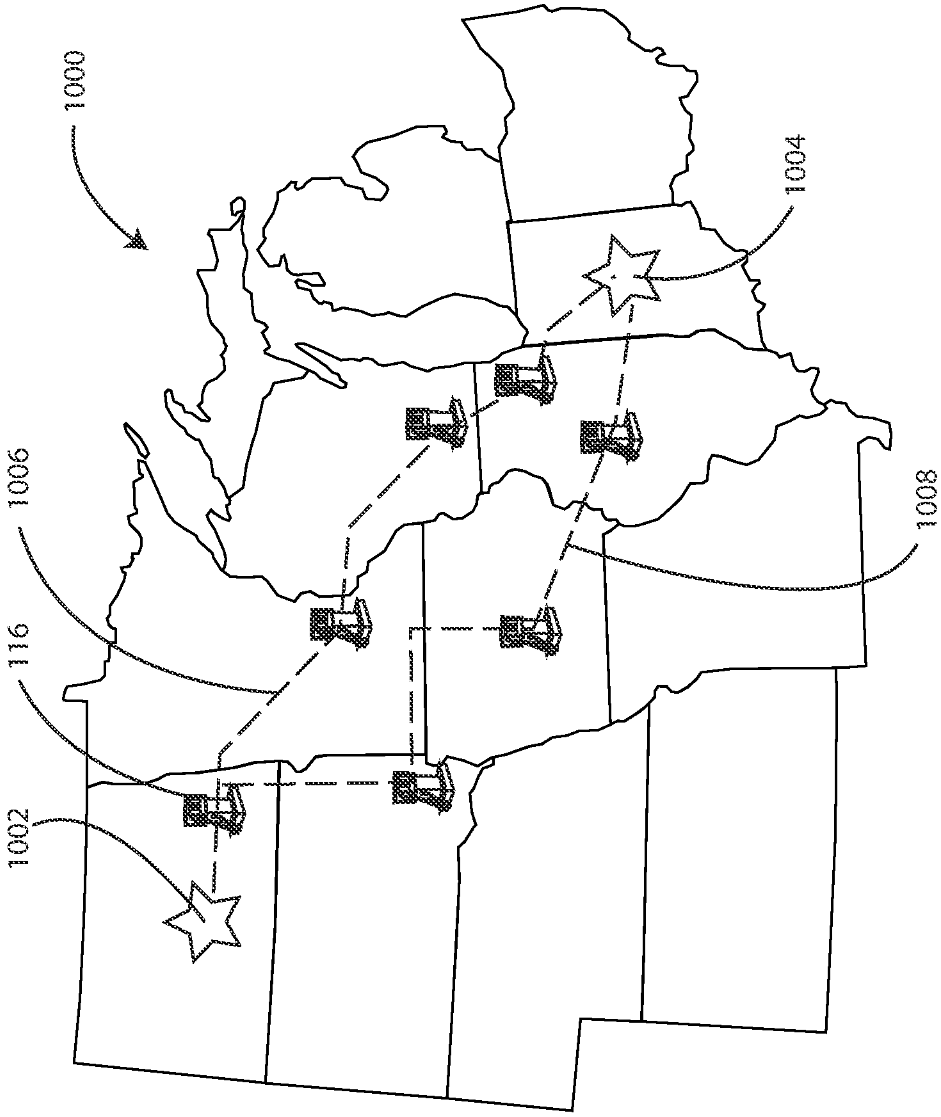
FIG. 10 is a schematic diagram illustrating two different routes between two geographic points and fueling locations along the routes in accordance with various embodiments herein.

In some embodiments, recommendations or guidance to a vehicle driver or fleet controller can be provided in the form of a map and/or data to populate or render a map on a device. Referring now to FIG. 10, a schematic diagram is shown illustrating two different routes between two geographic points and fueling locations along the routes in accordance with various embodiments herein. A map 1000 can be displayed by the system can display a starting location 1002 and an ending location 1004 (or destination). The map 1000 can further display a first route 1006 and a second route 1008 along with refueling locations 116 (all refueling locations or, in some cases, only recommended fueling locations) along the routes. In various embodiments, the system can be configured to calculate a cost of both routes including consideration of factors such as filter loading rates, distance travelled, time required for travel (speed), weather, availability of maintenance sites, availability of parts, price of fuel at refueling locations along the route, and the like.

In various embodiments, the system can be configured to calculate a remaining distance to recommended fueling stations, compare the remaining distance to a remaining vehicle range based on a remaining fuel level, and alert a vehicle driver or fleet operator if they leave, or are within a fixed distance of leaving, the range of the recommended refueling stations. The remaining distance to recommended fueling stations can be calculated by taking the current location of the vehicle and then comparing the same with a database including locations of recommended refueling locations (fueling stations). For all recommended fueling locations or for each recommended fueling location that falls within a set of those likely to be the closest (such as the top 5, 10, or 20 based on coordinates) a more precise distance can be calculated by using a distance calculation API such as the "Distance Matrix API" commercially available as part of the Google Maps Platform to select that which is closest based on distance that must be traveled.

In some embodiments, the shortest distance can be compared with a remaining range of the vehicle (such as fuel level times fuel mileage) and then an alert can be generated and sent to a vehicle operator and/or a fleet operator when they are within a fixed distance (50, 40, 30, 20, 10, 5, 1, or 0 miles) of hitting the point where remaining range of the vehicle is less than the distance to the nearest recommended fueling station. In various embodiments, the system can be further configured to query a database of filter providers, calculate a distance to the filter providers, compute a remaining useful life of a current fuel filter 208, and alert a vehicle 102 driver if the remaining useful life of the current fuel filter 208 may be insufficient to reach at least one of the filter providers. In various embodiments, the system can be further configured to calculate an optimal location for a filter service vendor to meet a vehicle 102 in need of fuel filter 208 service based on the vehicle's planned route, minimizing the travel time of the service provider, and ensuring the filter can be changed before it reaches the end of its useful life.

In various embodiments, a service guidance system can be included herein. The system can include a system control circuit. The system can be configured to calculate an optimal location for a filter service vendor to meet a vehicle in need of fuel filter service based on the vehicle's planned route, minimizing the travel time of the service provider, and ensuring the filter is changed before it reaches the end of its useful life. This can be done by calculating remaining filter life as described elsewhere herein and then determining a point along the currently planned route corresponding to when the remaining filter life will be exhausted (including or not including a safety margin of distance). For example, if it is determined that a currently used fuel filter has approximately 200 kilometers of remaining life then a point along the currently planned route of the vehicle approximately 200 kilometers (or less if a safety factor is applied) away from the current location can be determined. Then a routing API, such as the "Directions API" commercially available as part of the Google Maps Platform, can be used (e.g., data can be sent to it and received from it) in order to calculate a route for the filter service vendor to take in order to meet the vehicle in need of fuel filter service. The timing can also be evaluated. For example, if at average speeds the 200 kilometers is determined to take 2.5 hours, then the filter service vendor can be directed to proceed to the calculated meeting point in 2.5 hours.

In some embodiments, a service guidance system can be included herein including a system control circuit and wherein the system is configured to calculate an optimal route to a filter service vendor (which could be, for example, a fixed location such as a bricks and mortar service station) based on a vehicle's planned route, minimizing the travel time of the vehicle, and ensuring the filter is changed before it reaches the end of its useful life. In some embodiments, a vehicle guidance system is included herein including a system control circuit, wherein the system is configured to calculate an optimal route to a destination taking into account a location of a filter service vendor, minimizing the travel time of the vehicle, and ensuring the filter is changed before it reaches the end of its useful life. In some embodiments, the system is configured to optimize a preexisting planned route of a vehicle taking into account a location of a filter service vendor, minimizing the travel time of the vehicle, and ensuring the filter is changed before it reaches the end of its useful life.

In some cases, analysis of refueling locations to determine which may have adverse impacts on fuel filter loading can be triggered by or keyed upon the identification of an abnormal filter loading curve such as the start of an abnormal filter loading curve.

Figure 11:
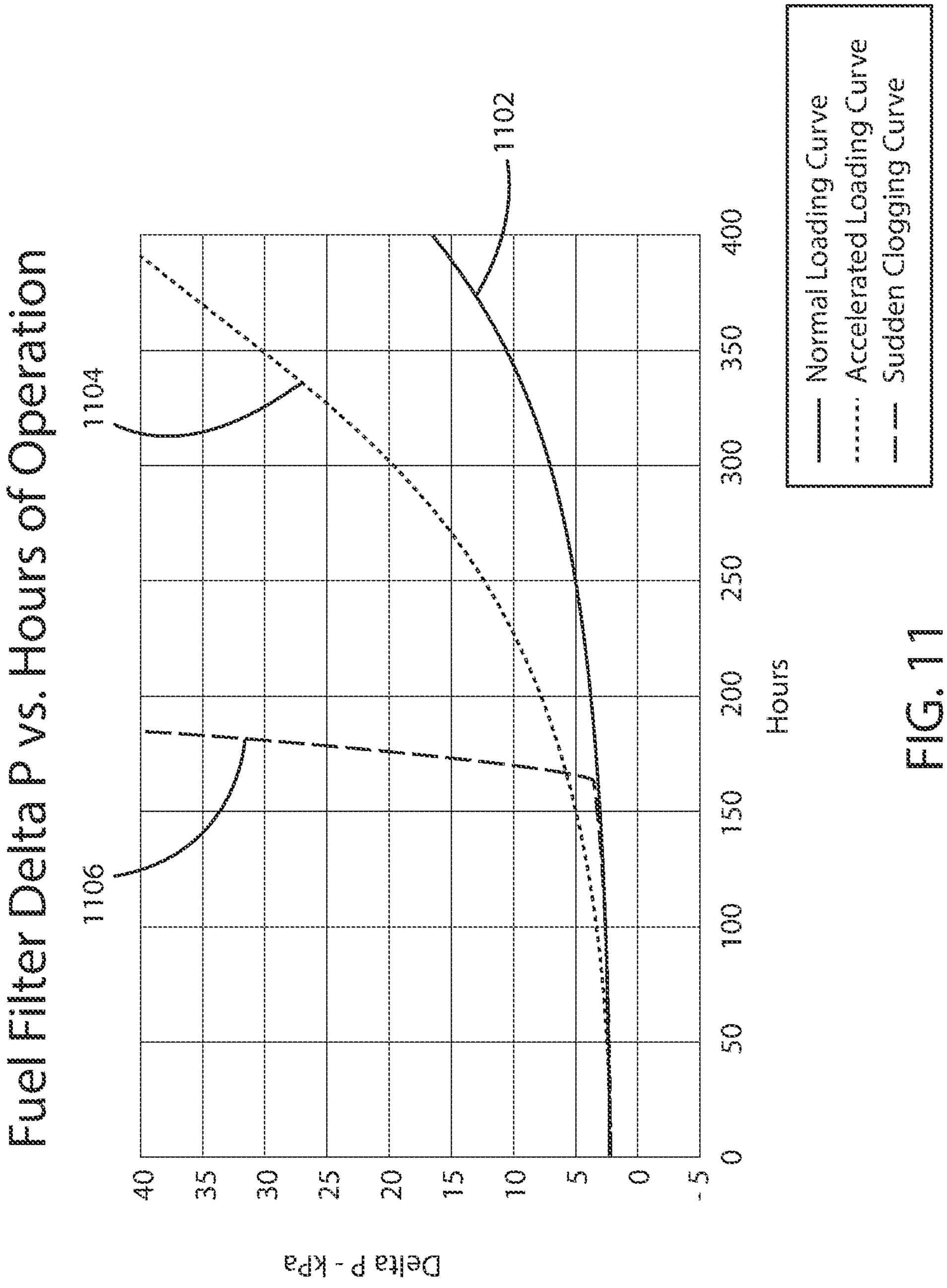
FIG. 11 is a graph showing fuel filter pressure drop versus bours of use for different types of loading curves.

Referring now to FIG. 11, a graph is shown of fuel filter pressure drop versus hours of use illustrating different types of idealized filter loading curves. In specific, FIG. 11 illustrates a normal loading curve 1102 characterized by a relatively flat initial growth of pressure drop (delta P) followed by steeper growth of pressure drop later in the life of the filter. FIG. 11 also illustrates two types of abnormal filter loading curves. In specific, FIG. 11 illustrates an accelerated loading curve 1104 and a sudden clogging curve 1106. The accelerated loading curve 1104 may be caused by contaminants (debris, dirt, glycerin, etc.) within the fuel. The accelerated loading curve 1104 assumes the same overall shape as the normal loading curve 1102, however it features a more rapid increase to higher pressure drop values. While FIG. 11 specifically shows pressure drop, it will be appreciated that other measure of filter restriction can exhibit similar patterns.

The sudden clogging curve 1106 may be caused by factors such as extremely contaminated fuel and/or an adverse reaction between components within fuels having different formulations (e.g., fuel chemistry) or additives (such as drying agents, corrosions inhibitors, etc.) leading to materials precipitating out of solution or other particulates being formed. Particulates/precipitates can include, but are not limited to, amine carboxylates, metal carboxylates, and other compounds or salts.

It will be appreciated that the filter loading curves shown in FIG. 11 are idealized. Further, the accelerated loading curve 1104 is representative of a particular level of contamination/impurities and will change depending upon the amounts of the same with higher levels of contamination/impurities resulting in faster loading. However, in some embodiments, specific filter loading curves can be stored within the system (such as saved within memory and/or a database) to serve as archetype (or template) filter loading curves. For example, the system may have a plurality of different archetype filter loading curves, such as 2, 3, 4, 5, 6, 8, 10, 15, 20, 30, 40, 50, 60 or more that correspond to different filter loading scenarios that are encountered in the field. The loading curves shown in FIG. 11 can serve as three specific examples of curves that could be used as archetypes. Then an observed filter loading curve can be matched against the set of archetype curves to determine which is the best match. Pattern matching and/or curve fitting techniques can be used to determine which is the best match. In some embodiments, a least squares-based approach can be used. In some embodiments, a machine-learning based approach (described in further detail below) can be used. Once an archetype or template filter loading curve has been found, prediction can be performed based on extrapolation using the identified archetype or template filter loading curve.

In various embodiments herein, the effect of specific refueling locations on fuel filter loading can be determined based on an effect on a filter loading curve. In various embodiments, the system can be configured to distinguish between a normal filter loading curve and an abnormal filter loading curve. In various embodiments, the system can specifically be configured to distinguish between a normal filter loading curve, an accelerated filter loading curve, and a sudden clogging curve. Aspects that can be used to distinguish such curves can include, but are not limited to, maximum or average observed rate of change in filter restriction (such as pressure drop or another measure) and maximum or average observed rate of change in filter restriction (such as pressure drop or another measure) for a given amount of distance the fuel filter has been in use. In various embodiments, filter loading curves with a maximum rate of range (slope) exceeding a threshold value are deemed abnormal. In various embodiments, filter loading curves with a maximum rate of range (slope) exceeding a threshold value for a particular degree of use (distance and/or hours) are deemed abnormal. In various embodiments, multiple thresholds can be use. For example, filter loading curves with a maximum rate of range (slope) exceeding a first threshold value (with or without consideration of distance and/or hours of use) are deemed abnormal and then further deemed to be a sudden clogging curve if the maximum rate of change also exceeds a second threshold value or an accelerated loading curve if the maximum rate of change does not exceed the second threshold value.

In some embodiments, the system can be configured to identify a refueling location and/or pattern of refueling locations visited immediately before an abnormal filter loading curve begins. In various embodiments, the system can be configured to identify a refueling location and/or pattern of refueling locations visited immediately before a filter loading curve changes to exhibit more rapid loading. In various embodiments, the system control circuit can be configured to determine sequences of refueling locations visited immediately before a sudden clogging curve begins. The determined sequence can include 2, 3, 4, 5, 6, 7, 8 or more prior refueling locations visited.

Various other steps can be taken after a particular refueling location is identified as possibly being the source of fuel leading to an abnormal fuel filter loading curve. In some embodiments, the system can classify an identified location and/or a pattern of identified locations as being a source (or possible source) of contaminated fuel and can store the classification in a refueling location database along with information regarding loading curves resulting from refueling at the specific refueling location. In various embodiments, the system can classify the identified location as being a source or possible source of contaminated fuel and then query a database for additional data regarding the identified location, such as any confirmatory data based on other refueling events that have been recorded (with positive or negative outcomes) regarding the same refueling location.

In some embodiments, a system herein can build and/or store a list of refueling locations that are known to be good (or approved) from the perspective of their impact fuel filter loading or otherwise. Similarly, in some embodiments, a system herein can build and/or store a list of refueling locations that are known to be bad from the perspective of their impact fuel filter loading or otherwise. For example, as the system classifies refueling locations as previously described it can add them to a data storage table that is part of the on-vehicle system itself and/or part of a remote data storage facility accessible through a data network. These listing(s) can then be accessed by system(s) that are part of the same vehicle in the future, by other vehicles that are managed by the same fleet management system, and/or by other vehicles that are not managed by the same fleet management system in order to provide system guidance regarding optimal refueling locations and/or be considered as a part of optimal vehicle route calculations described herein. In some cases, these listings can be further modified and/or annotated by other systems or operators for various purposes. As merely one example, these listings can be modified and/or annotated by a fleet manager for purposes of identifying those locations for which a contractual relationship may exist for the vehicle fleet regarding the provision of fuel.

Figure 12:
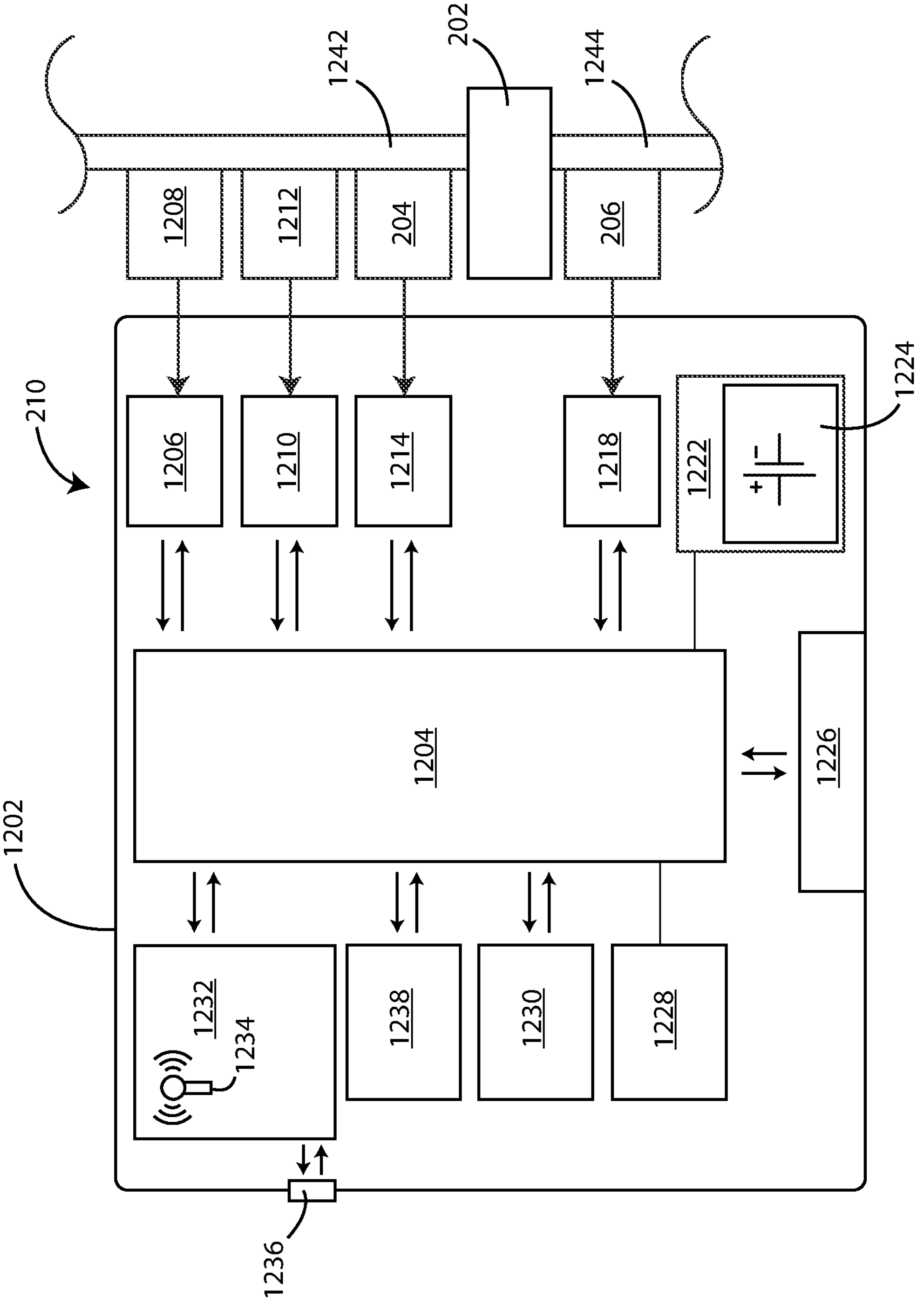
FIG. 12 is a block diagram of some components of a fuel monitoring system in accordance with various embodiments herein.

It will be appreciated that systems herein can include many different components. Referring now to FIG. 12, a block diagram is shown of some components of a fuel monitoring system in accordance with various embodiments herein. However, it will be appreciated that a greater or lesser number of components can be included with various embodiments and that this schematic diagram is merely illustrative. In specific, FIG. 12 shows a fuel filter monitoring device 210. The fuel filter monitoring device 210 can include a housing 1202 and a system control circuit 1204 or ("control circuit"). The control circuit 1204 can include various electronic components including, but not limited to, a microprocessor, a microcontroller, a FPGA (field programmable gate array) chip, an application specific integrated circuit (ASIC), or the like. The control circuit 1204 can execute various operations as described herein. However, it will be appreciated that operations herein can be executed across multiple devices with separate physical circuits, processors, or controllers with different operations being performed redundantly or divided across different physical devices. As such, some operations may be performed (in whole or in part) at the edge, such as by a circuit/processor/controller associated with a fuel filter monitoring device 210 while other operations may be performed (in whole or in part) by a separate device or in the cloud.

A fuel filter sensor device or sensor package of the system can include an upstream pressure sensor 204 that can be associated with an upstream portion of the fuel line 1242 and can be positioned upstream of the filter head unit 202 and/or as a part of the filter head unit 202, but upstream of the fuel filter. The upstream pressure sensor 204 can be in communication with an upstream pressure sensor channel interface 1214. The fuel filter sensor device can also include a downstream pressure sensor 206 that can be associated with a downstream portion of the fuel line 1244 and can be positioned downstream of the filter head unit 202 and/or as a part of the filter head unit 202, but downstream of the fuel filter. The downstream pressure sensor 206 can be in communication with a downstream pressure sensor channel interface 1218.

In various embodiments, the fuel filter monitoring device 210 can include and/or be in communication with a water-in-fuel sensor 1208 and a water-in-fuel sensor channel interface 1206. In various embodiments, the fuel filter monitoring device 210 can include and/or be in communication with another type of sensor, such as temperature sensor 1212 and a temperature sensor channel interface 1210. Other types of sensors herein can include vibration sensors, flow sensors, and the like.

The channel interfaces can include various components such as amplifiers, analog-to-digital converters (ADCs), digital-to-analog converters (DACs), digital signal processors (DSPs), filters (high-pass, low-pass, band-pass) and the like. In some cases, the channel interfaces may not exist as discrete components but, rather, can be integrated into the control circuit 1204.

Temperature sensors herein can be of various types. In some embodiments, the temperature sensor 1212 can be a thermistor, a resistance temperature device (RTD), a thermocouple, a semiconductor temperature sensor, or the like.

Pressure sensors herein can be of various types. The pressure sensors 204, 206 can include, but are not limited to, strain gauge type pressure sensors, capacitive type pressure sensors, piezoelectric type pressure sensors, and the like. In some embodiments, pressure sensors herein can be MEMS-based pressure sensors. In various embodiments, the pressure sensor can be a high-speed (e.g., high sample rate) pressure sensor. In various embodiments the high-speed pressure sensor can sample at rates of 1,000, 1,500, 2,000, 2,500, 3,000, 5,000, 10,000, 15,000, 20,000 Hz or higher, or at a rate falling within a range between any of the foregoing. In various embodiments the high-speed pressure sensor can have a response time of less than 10, 5, 2.5, 1, 0.5, 0.25, 0.1, 0.05 or 0.01 milliseconds, or a response time falling within a range between any of the foregoing.

The processing power of the control circuit 1204 and components thereof can be sufficient to perform various operations including various operations on signals/data from sensors (such as sensors 204, 206, 1208, and 1212) including, but not limited to averaging, time-averaging, statistical analysis, normalizing, aggregating, sorting, deleting, traversing, transforming, condensing (such as eliminating selected data and/or converting the data to a less granular form), compressing (such as using a compression algorithm), merging, inserting, time-stamping, filtering, discarding outliers, calculating trends and trendlines (linear, logarithmic, polynomial, power, exponential, moving average, etc.), normalizing data/signals, and the like. Fourier analysis can decompose a physical signal into a number of discrete frequencies, or a spectrum of frequencies over a continuous range. In various embodiments herein, operations on signals/data can include Fast Fourier Transformations (FFT) to convert data/signals from a time domain to a frequency domain. Other operations on signals/data here can include spectral estimation, frequency domain analysis, calculation of root mean square acceleration value (GRMS), calculation of acceleration spectral density, power spectral densities, Fourier series, Z transforms, resonant frequency determination, harmonic frequency determination, and the like. It will be appreciated that while various of the operations described herein (such as Fast Fourier transforms) can be performed by general-purpose microprocessors, they can also be performed more efficiently by digital signal processors (DSPs) which can, in some embodiments, be integrated with the control circuit 1204 or may exist as separate, discrete components.

In various embodiments herein, machine learning algorithms can be used to derive the relationship between specific refueling locations and effects on filter loading behavior. Also, in various embodiments herein, machine learning algorithms can be used to match an observed filter loading curve against previously stored filter loading curves (such as pattern matching against archetype curves) in order to identify the type of loading curve that is observed and/or predict the future effects of such a curve. Machine learning algorithms used herein can include, but are not limited to, supervised learning and unsupervised learning algorithms.

Machine learning algorithms used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Machine learning algorithms herein can also include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms herein can include categorical mixture models, deep learning methods, hierarchical clustering, K-means clustering, correlation clustering, and kernel principal component analysis. Ensemble learning algorithms herein can include boosting, bootstrap aggregating, ensemble averaging, and mixture of experts. General algorithms for predicting arbitrarily-structured sets of labels herein can include Bayesian networks and Markov random fields. Multilinear subspace learning algorithms herein can include multilinear principal component analysis (MPCA). Real-valued sequence labeling algorithms can include Kalman filters and particle filters. Regression algorithms herein can include both supervised (such as Gaussian process regression, linear regression, neural networks and deep learning methods) and unsupervised (such as independent component analysis and principal components analysis) approaches. Sequence labeling algorithms herein can include both supervised (such as conditional random fields, hidden Markov models, maximum entropy Markov models, and recurrent neural networks) and unsupervised (hidden Markov models and dynamic time warping) approaches.

In various embodiments, the fuel filter monitoring device 210 can include a power supply circuit 1222. In some embodiments, the power supply circuit 1222 can include various components including, but not limited to, a battery 1224, a capacitor, a power-receiver such as a wireless power receiver, a transformer, a rectifier, and the like.

In various embodiments the fuel filter monitoring device 210 can include an output device 1226. The output device 1226 can include various components for visual and/or audio output including, but not limited to, lights (such as LED lights), a display screen, a speaker, and the like. In some embodiments, the output device can be used to provide notifications or alerts to a system user such as current system status, an indication of a problem, a required user intervention, a proper time to perform a maintenance action, or the like.

In various embodiments the fuel filter monitoring device 210 can include memory 1228 and/or a memory controller. The memory can include various types of memory components including dynamic RAM (D-RAM), read only memory (ROM), static RAM (S-RAM), disk storage, flash memory, EEPROM, battery-backed RAM such as S-RAM or D-RAM and any other type of digital data storage component. In some embodiments, the electronic circuit or electronic component includes volatile memory. In some embodiments, the electronic circuit or electronic component includes non-volatile memory. In some embodiments, the electronic circuit or electronic component can include transistors interconnected to provide positive feedback operating as latches or flip flops, providing for circuits that have two or more metastable states, and remain in one of these states until changed by an external input. Data storage can be based on such flip-flop containing circuits. Data storage can also be based on the storage of charge in a capacitor or on other principles. In some embodiments, the non-volatile memory 1228 can be integrated with the control circuit 1204.

In various embodiments the fuel filter monitoring device 210 can include a clock circuit 1230. In some embodiments, the clock circuit 1230 can be integrated with the control circuit 1204. While not shown in FIG. 12, it will be appreciated that various embodiments herein can include a data/communication bus to provide for the transportation of data between components such as an I2C, a serial peripheral interface (SPI), a universal asynchronous receiver/transmitter (UART), or the like. In some embodiments, an analog signal interface can be included. In some embodiments, a digital signal interface can be included.

In various embodiment the fuel filter monitoring device 210 can include a communications circuit 1232. In various embodiments, the communications circuit can include components such as an antenna 1234, amplifiers, filters, digital to analog and/or analog to digital converters, and the like. In some embodiments, the fuel filter monitoring device 210 can also include wired input/out interface 1236 for wired communication with other systems/components including, but not limited to one or more vehicle ECUs, a CANBus network (controller area network), or the like.

The fuel monitoring system for a vehicle can also include a geolocation circuit 1238. In various embodiments, the geolocation circuit 1238 can be configured to generate or receive geolocation data. In various embodiments, the geolocation circuit 1238 can receive geolocation data from a separate device. In various embodiments, the geolocation circuit 1238 can infer geolocation based on detection of a wireless signal (such as a WIFI signal, a cell tower signal, or the like). In various embodiments, the geolocation circuit 1238 can include a satellite communications circuit.

The system and/or the system control circuit 1204 can be configured to make various calculations as described herein. For example, in various embodiments, the system control circuit 1204 can be further configured to estimate expected loading rate associated with refueling at a particular refueling location 116 based on previously observed fuel filter 208 loading. In various embodiments, the system control circuit 1204 can be further configured to calculate a cost associated with a particular refueling location 116 based on estimated expected fuel filter 208 loading rate. In various embodiments, the system control circuit 1204 can be further configured to generate a listing of recommended and dis-recommended fueling stations. In various embodiments, the system control circuit 1204 can be further configured to generate an alert for a vehicle 102 driver if the vehicle 102 enters the location of a dis-recommended fueling station. In various embodiments, the system control circuit 1204 can be further configured to generate a report that profiles the frequency with which different drivers in a fleet use recommended and dis-recommended fueling stations. In various embodiments, the system control circuit 1204 configured to distinguish between a normal filter loading curve. In various embodiments, the system control circuit 1204 configured to distinguish between a normal filter loading curve and an abnormal filter loading curve. In various embodiments, the system control circuit 1204 can be configured to identify a refueling location 116 visited immediately before an abnormal filter loading curve begins. In various embodiments, the system control circuit 1204 can be configured to identify a refueling location 116 visited immediately before a filter loading curve changes to exhibit more rapid loading. In various embodiments, the system control circuit 1204 classifies the identified location as being a source of contaminated fuel and stores the classification in a refueling location 116 database. In various embodiments, the system control circuit 1204 can be further configured to generate a fuel system parts inventory recommendation based on the refueling location 116 database. In various embodiments, the system control circuit 1204 classifies the identified location as being a possible source of contaminated fuel and queries a database for additional data regarding the identified location. In various embodiments, the system control circuit 1204 can be configured to determine sequences of refueling locations visited immediately before a sudden clogging curve begins. In various embodiments, the system control circuit 1204 can be further configured to evaluate at least one of weather data, temperature data, pressure data, humidity data, fuel filter model number, engine model number, driver ID, and detected refueling times to identify the effect of specific refueling locations on fuel filter loading. In various embodiments, the system control circuit 1204 further configured to evaluate data from the water-in-fuel sensor and correlate refueling locations with subsequent changes in the data from the water-in-fuel sensor to identify an effect of specific refueling locations on water-in-fuel sensor data.

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of monitoring fuel systems can include measuring filter restriction, identifying refueling locations based on fuel level data and geolocation data, and calculating an impact of specific refueling locations on fuel filter loading by evaluating filter restriction trends after refueling at refueling locations.

In an embodiment, the method can further include estimating expected loading rate associated with refueling at a particular refueling location based on previously observed fuel filter loading. In an embodiment, the method can further include calculating a cost associated with a particular refueling location based on estimated expected fuel filter loading rate.

In an embodiment, the method can further include generating a recommendation can include a recommended refueling location. In an embodiment, the method can further include forwarding the recommendation to a mobile communications device associated with a vehicle or a driver of a vehicle. In an embodiment of the method, the recommendation is generated including consideration of fuel system parts inventory at refueling locations. In an embodiment, the method can further include generating a recommendation can include a recommended refueling time. In an embodiment, the method can further include generating a recommendation can include a recommended refueling location and a recommended refueling time. In an embodiment, the method can further include forwarding the recommendation to a mobile communications device associated with a vehicle or a driver of a vehicle.

In an embodiment, the method can further include generating a listing of recommended and dis-recommended fueling stations. In an embodiment, the method can further include generating an alert for a vehicle driver if the vehicle enters the location of a dis-recommended fueling station. In an embodiment, the method can further include generating a report that profiles the frequency with which different drivers in a fleet use recommended and dis-recommended fueling stations.

In an embodiment, the method can further include distinguishing between a normal filter loading curve, an accelerated filter loading curve, and a sudden clogging curve. In an embodiment, the method can further include distinguishing between a normal filter loading curve and an abnormal filter loading curve.

In an embodiment, the method can further include identifying a refueling location visited immediately before an abnormal filter loading curve begins. In an embodiment, the method can further include identifying a refueling location visited immediately before a filter loading curve changes to exhibit more rapid loading.

In an embodiment, the method can further include classifying the identified location as being a source of contaminated fuel and stores the classification in a refueling location database.

In an embodiment, the method can further include generating a fuel system parts inventory recommendation based on the refueling location database. In an embodiment of the method, the fuel system parts inventory recommendation includes a recommendation to increase an inventory of fuel filters at refueling locations that occur in a sequence of refueling locations after an identified location with contaminated fuel.

In an embodiment, the method can further include classifying the identified location as being a possible source of contaminated fuel and querying a database for additional data regarding the identified location.

In an embodiment, the method can further include determining sequences of refueling locations visited immediately before a sudden clogging curve begins.

In an embodiment, the method can further include evaluating one or more of weather data, temperature data, pressure data, humidity data, fuel filter model number, engine model number, driver ID, and detected refueling times to identify the effect of specific refueling locations on fuel filter loading.

In an embodiment, identifying refueling locations based on fuel level data and geolocation data comprises identifying a geolocation at a time of a fuel level increase.

In an embodiment, the method can further include evaluating data from a water-in-fuel sensor and identifying an effect of specific refueling locations on water-in-fuel sensor data.

In an embodiment, the method can further include estimating remaining fuel filter life taking into account refueling locations used.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A fuel monitoring system for a vehicle comprising:

a fuel filter sensor device configured to generate data reflecting a filter restriction value of a fuel filter;

a geolocation circuit configured to generate or receive geolocation data;

a system control circuit configured to evaluate the fuel filter sensor device data to determine changes in the filter restriction value;

receive fuel level data;

cross-reference geolocation data and fuel level data to identify refueling locations utilized;

correlate refueling locations with subsequent changes in the filter restriction value to identify an effect of specific refueling locations utilized on fuel filter loading; and generate an alert for a vehicle driver if the vehicle enters a location of a dis-recommended fueling station.

2. The fuel monitoring system of claim 1, wherein the system control circuit is further configured to estimate an expected loading rate associated with refueling at a particular refueling location based on previously observed fuel filter loading.

3. The fuel monitoring system of claim 1, wherein the system control circuit is further configured to calculate a cost associated with a particular refueling location based on estimated expected fuel filter loading rate.

4. The fuel monitoring system of claim 1, wherein the system control circuit is further configured to generate a recommendation comprising a recommended refueling location.

5. The fuel monitoring system of claim 1, wherein the system control circuit is further configured to generate a recommendation comprising a recommended refueling time.

6. The fuel monitoring system of claim 1, wherein the system control circuit is further configured to generate a recommendation comprising a recommended refueling location and a recommended refueling time.

7. The fuel monitoring system of claim 1, wherein the system control circuit is further configured to generate a listing of recommended and dis-recommended fueling stations.

8. The fuel monitoring system of claim 1, wherein the system control circuit is further configured to generate a report that profiles the frequency with which different drivers in a fleet use recommended and dis-recommended fueling stations.

9. The fuel monitoring system of claim 1, wherein the effect of specific refueling locations on fuel filter loading is determined based on an effect on a filter loading curve.

10. The fuel monitoring system of claim 9, the system control circuit configured to distinguish between a normal filter loading curve, an accelerated filter loading curve, and a sudden clogging curve.

11. The fuel monitoring system of claim 9, the system control circuit configured to distinguish between a normal filter loading curve and an abnormal filter loading curve.

12. The fuel monitoring system of claim 1, wherein the system control circuit is configured to identify a refueling location visited immediately before a filter loading curve changes to exhibit more rapid loading.

13. The fuel monitoring system of claim 1, wherein the system control circuit is further configured to evaluate one or more of weather data, temperature data, pressure data, humidity data, fuel filter model number, engine model number, driver ID, and detected refueling times to identify the effect of specific refueling locations on fuel filter loading.

14. The fuel monitoring system of claim 1, further comprising a water-in-fuel sensor, the system control circuit further configured to evaluate data from the water-in-fuel sensor and correlate refueling locations with subsequent changes in the data from the water-in-fuel sensor to identify an effect of specific refueling locations on water-in-fuel sensor data.

15. The fuel monitoring system of claim 1, further comprising a particulate counter, the system control circuit further configured to evaluate data from the particulate counter and correlate refueling locations with subsequent changes in the data from the particulate counter to identify an effect of specific refueling locations on particulate counter data.

16. A fuel monitoring system for a vehicle comprising:

a fuel filter sensor device configured to generate data reflecting a filter restriction value of a fuel filter, the fuel filter sensor device comprising:

an upstream pressure sensor configured to sense a first pressure in a fuel line upstream of a fuel filter; and a downstream pressure sensor configured to sense a second pressure in the fuel line downstream of the fuel filter;

a geolocation circuit configured to generate or receive geolocation data;

a system control circuit configured to evaluate the fuel filter sensor device data to determine changes in the filter restriction value, wherein the filter restriction value comprises a pressure drop across the fuel filter calculated from the first pressure and the second pressure;

receive fuel level data;

cross-reference geolocation data and fuel level data to identify refueling locations utilized;

correlate refueling locations with subsequent changes in the filter restriction value to identify an effect of specific refueling locations utilized on fuel filter loading.

17. A fuel monitoring system for a vehicle comprising:

a fuel filter sensor device configured to generate data reflecting a filter restriction value of a fuel filter, the fuel filter sensor device comprising a differential pressure sensor configured to measure a pressure drop across a fuel filter;

a geolocation circuit configured to generate or receive geolocation data;

a system control circuit configured to evaluate the fuel filter sensor device data to determine changes in the filter restriction value;

determine a fuel filter change event based on a reduction in the pressure drop across the fuel filter exceeding a threshold percent reduction;

receive fuel level data;

cross-reference geolocation data and fuel level data to identify refueling locations utilized;

correlate refueling locations with subsequent changes in the filter restriction value to identify an effect of specific refueling locations utilized on fuel filter loading.

18. The fuel monitoring system of claim 17, wherein the threshold percent reduction is a 20% reduction in the pressure drop across the fuel filter.

* * * * *